United States Patent
McCarthy et al.

(10) Patent No.: US 8,932,284 B2
(45) Date of Patent: *Jan. 13, 2015

(54) METHODS OF DETERMINING TISSUE TEMPERATURES IN ENERGY DELIVERY PROCEDURES

(71) Applicant: Advanced Cardiac Therapeutics, Inc., Menlo Park, CA (US)

(72) Inventors: John F. McCarthy, Newbury, NH (US); Timothy J. Lenihan, Hradec Kralove (CZ); Eric R. Kanowsky, Santa Barbara, CA (US); Robert C. Allison, Rancho Palos Verdes, CA (US)

(73) Assignees: Advanced Cardiac Therapeutics, Inc., Santa Clara, CA (US); Meridian Medical Systems, LLC, Portland, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/274,407

(22) Filed: May 9, 2014

(65) Prior Publication Data

US 2014/0303614 A1    Oct. 9, 2014

Related U.S. Application Data

(63) Continuation of application No. 13/368,112, filed on Feb. 7, 2012.

(51) Int. Cl.
*A61B 18/04* (2006.01)
*A61B 18/12* (2006.01)
(Continued)

(52) U.S. Cl.
CPC ......... *A61B 18/1492* (2013.01); *A61B 18/1206* (2013.01); *A61B 2018/00577* (2013.01); *A61B 2018/00791* (2013.01); *A61B 18/02* (2013.01); *A61B 2018/00029* (2013.01)
USPC .......................................................... 606/34

(58) Field of Classification Search
CPC ............... A61B 18/12; A61B 18/1206; A61B 18/1815; A61B 18/1482; A61B 18/24; A61B 18/28; A61B 18/18
USPC .......................................................... 606/34
See application file for complete search history.

(56) References Cited

U.S. PATENT DOCUMENTS 4,190,053 A    2/1980    Sterzer
4,197,860 A    4/1980    Sterzer
(Continued)

FOREIGN PATENT DOCUMENTS

EP    0746372 B1    5/2003
EP    1803407 A1    7/2007
(Continued)

OTHER PUBLICATIONS

Arunachalam et al., "Characterization of a digital microwave radiometry system for noninvasive thermometry using temperature controlled homogeneous test load," Phys. Med. Biol. 53(14): 3883-3901, Jul. 21, 2008.
(Continued)

*Primary Examiner* — George Manuel
(74) *Attorney, Agent, or Firm* — Knobbe, Martens, Olson & Bear LLP

(57) ABSTRACT

Methods and systems for treating tissue that employ a radiometer for measurement and/or control are provided. For example, methods and systems are provided for radiometrically measuring temperature, such as by calculating temperature based on signal(s) from a radiometer, thereby providing useful information about tissue temperature at depth, even during an optional irrigated procedure.

20 Claims, 15 Drawing Sheets

(51) Int. Cl.
*A61B 18/14* (2006.01)
*A61B 18/02* (2006.01)
*A61B 18/00* (2006.01)

(56) References Cited

U.S. PATENT DOCUMENTS

| | | | |
|---|---|---|---|
| 4,346,716 A | 8/1982 | Carr | |
| 4,557,272 A | 12/1985 | Carr | |
| 4,632,127 A | 12/1986 | Sterzer | |
| 4,647,281 A | 3/1987 | Carr | |
| 4,715,727 A | 12/1987 | Carr | |
| 4,774,961 A | 10/1988 | Carr | |
| 4,815,479 A | 3/1989 | Carr | |
| 4,945,912 A | 8/1990 | Langberg | |
| 5,073,167 A | 12/1991 | Carr et al. | |
| 5,105,808 A | 4/1992 | Neuwirth et al. | |
| 5,149,198 A | 9/1992 | Sterzer | |
| 5,176,146 A | 1/1993 | Chive et al. | |
| 5,198,776 A | 3/1993 | Carr | |
| 5,334,141 A | 8/1994 | Carr et al. | |
| 5,344,435 A | 9/1994 | Turner et al. | |
| 5,354,325 A | 10/1994 | Chive et al. | |
| 5,364,336 A | 11/1994 | Carr | |
| 5,370,676 A | 12/1994 | Sozanski et al. | |
| 5,383,874 A | 1/1995 | Jackson et al. | |
| 5,456,682 A | 10/1995 | Edwards et al. | |
| 5,462,521 A | 10/1995 | Brucker et al. | |
| 5,514,130 A | 5/1996 | Baker | |
| 5,531,662 A | 7/1996 | Carr | |
| 5,549,639 A | 8/1996 | Ross | |
| 5,584,830 A | 12/1996 | Ladd et al. | |
| 5,591,125 A | 1/1997 | Edwards et al. | |
| 5,616,268 A | 4/1997 | Carr | |
| 5,624,392 A | 4/1997 | Saab | |
| 5,643,197 A | 7/1997 | Brucker et al. | |
| 5,651,780 A | 7/1997 | Jackson et al. | |
| 5,662,110 A | 9/1997 | Carr | |
| 5,683,381 A | 11/1997 | Carr et al. | |
| 5,683,382 A | 11/1997 | Lenihan et al. | |
| 5,688,050 A | 11/1997 | Sterzer et al. | |
| 5,688,267 A | 11/1997 | Panescu et al. | |
| 5,690,614 A | 11/1997 | Carr et al. | |
| 5,702,386 A | 12/1997 | Stern et al. | |
| 5,743,903 A | 4/1998 | Stern et al. | |
| 5,779,635 A | 7/1998 | Carr | |
| 5,782,897 A | 7/1998 | Carr | |
| 5,792,140 A | 8/1998 | Tu et al. | |
| 5,800,432 A | 9/1998 | Swanson | |
| 5,807,395 A | 9/1998 | Mulier et al. | |
| 5,833,688 A | 11/1998 | Sieben et al. | |
| 5,849,028 A | 12/1998 | Chen | |
| 5,863,290 A | 1/1999 | Gough et al. | |
| 5,868,743 A | 2/1999 | Saul et al. | |
| 5,876,340 A | 3/1999 | Tu et al. | |
| 5,879,349 A | 3/1999 | Edwards | |
| 5,893,885 A | 4/1999 | Webster, Jr. | |
| 5,904,709 A | 5/1999 | Arndt et al. | |
| 5,906,614 A | 5/1999 | Stern et al. | |
| 5,913,856 A | 6/1999 | Chia et al. | |
| 5,919,218 A | 7/1999 | Carr | |
| 5,935,063 A | 8/1999 | Nguyen | |
| 5,938,658 A | 8/1999 | Tu | |
| 5,938,659 A | 8/1999 | Tu et al. | |
| 5,948,009 A | 9/1999 | Tu | |
| 5,954,719 A | 9/1999 | Chen et al. | |
| 5,971,980 A | 10/1999 | Sherman | |
| 5,974,343 A | 10/1999 | Brevard et al. | |
| 5,983,124 A | 11/1999 | Carr | |
| 5,992,419 A | 11/1999 | Sterzer et al. | |
| 5,997,534 A | 12/1999 | Tu et al. | |
| 6,006,123 A | 12/1999 | Nguyen et al. | |
| 6,113,593 A | 9/2000 | Tu et al. | |
| 6,123,703 A | 9/2000 | Tu et al. | |
| 6,146,359 A | 11/2000 | Carr et al. | |
| 6,210,367 B1 | 4/2001 | Carr | |
| 6,210,406 B1 | 4/2001 | Webster | |
| 6,217,576 B1 | 4/2001 | Tu et al. | |
| 6,230,060 B1 | 5/2001 | Mawhinney | |
| 6,235,022 B1 | 5/2001 | Hallock et al. | |
| 6,259,941 B1 | 7/2001 | Chia et al. | |
| 6,277,113 B1 | 8/2001 | Berube | |
| 6,283,962 B1 | 9/2001 | Tu et al. | |
| 6,346,104 B2 | 2/2002 | Daly et al. | |
| 6,352,534 B1 | 3/2002 | Paddock et al. | |
| 6,371,955 B1 | 4/2002 | Fuimaono et al. | |
| 6,402,739 B1 | 6/2002 | Neev | |
| 6,402,742 B1 | 6/2002 | Blewett et al. | |
| 6,405,067 B1 | 6/2002 | Mest et al. | |
| 6,423,057 B1 | 7/2002 | He et al. | |
| 6,424,869 B1 | 7/2002 | Carr et al. | |
| 6,458,123 B1 | 10/2002 | Brucker et al. | |
| 6,477,396 B1 | 11/2002 | Mest et al. | |
| 6,477,426 B1 | 11/2002 | Fenn et al. | |
| 6,482,203 B2 | 11/2002 | Paddock et al. | |
| 6,490,488 B1 | 12/2002 | Rudie et al. | |
| 6,496,738 B2 | 12/2002 | Carr | |
| 6,522,930 B1 | 2/2003 | Schaer et al. | |
| 6,537,272 B2 | 3/2003 | Christopherson et al. | |
| 6,579,288 B1 | 6/2003 | Swanson et al. | |
| 6,587,732 B1 | 7/2003 | Carr | |
| 6,602,242 B1 | 8/2003 | Fung et al. | |
| 6,611,699 B2 | 8/2003 | Messing | |
| 6,669,692 B1 | 12/2003 | Nelson et al. | |
| 6,699,241 B2 | 3/2004 | Rappaport et al. | |
| 6,752,805 B2 | 6/2004 | Maguire et al. | |
| 6,847,848 B2 | 1/2005 | Sterzer et al. | |
| 6,852,120 B1 | 2/2005 | Fuimaono | |
| 6,887,238 B2 | 5/2005 | Jahns et al. | |
| 6,888,141 B2 | 5/2005 | Carr | |
| 6,905,495 B1 | 6/2005 | Fuimaono et al. | |
| 6,932,776 B2 | 8/2005 | Carr | |
| 6,949,095 B2 | 9/2005 | Vaska et al. | |
| 6,960,205 B2 | 11/2005 | Jahns et al. | |
| 6,974,455 B2 | 12/2005 | Garabedian et al. | |
| 6,986,769 B2 | 1/2006 | Nelson et al. | |
| 7,029,470 B2 | 4/2006 | Francischelli et al. | |
| 7,150,744 B2 | 12/2006 | Edwards et al. | |
| 7,163,537 B2 | 1/2007 | Lee et al. | |
| 7,175,734 B2 | 2/2007 | Stewart et al. | |
| 7,197,356 B2 | 3/2007 | Carr | |
| 7,263,398 B2 | 8/2007 | Carr | |
| 7,276,061 B2 | 10/2007 | Schaer et al. | |
| 7,285,116 B2 | 10/2007 | de la Rama et al. | |
| 7,303,558 B2 | 12/2007 | Swanson | |
| 7,326,235 B2 | 2/2008 | Edwards | |
| 7,331,960 B2 | 2/2008 | Schaer | |
| 7,367,972 B2 | 5/2008 | Francischelli et al. | |
| 7,582,050 B2 | 9/2009 | Schlorff et al. | |
| 7,588,568 B2 | 9/2009 | Fuimaono et al. | |
| 7,588,658 B2 | 9/2009 | Yamamoto et al. | |
| 7,623,899 B2 | 11/2009 | Worley et al. | |
| 7,628,788 B2 | 12/2009 | Datta | |
| 7,662,152 B2 | 2/2010 | Sharareh et al. | |
| 7,678,104 B2 | 3/2010 | Keidar | |
| 7,699,841 B2 | 4/2010 | Carr | |
| 7,727,230 B2 | 6/2010 | Fuimaono et al. | |
| 7,734,330 B2 | 6/2010 | Carr | |
| 7,761,148 B2 | 7/2010 | Fuimaono et al. | |
| 7,764,994 B2 | 7/2010 | Fuimaono et al. | |
| 7,769,469 B2 | 8/2010 | Carr et al. | |
| 7,771,420 B2 | 8/2010 | Butty et al. | |
| 7,794,460 B2 | 9/2010 | Mulier et al. | |
| 7,815,635 B2 | 10/2010 | Wittkampf et al. | |
| 7,824,399 B2 | 11/2010 | Francischelli et al. | |
| 7,826,904 B2 | 11/2010 | Appling et al. | |
| 7,857,809 B2 | 12/2010 | Drysen | |
| 7,857,810 B2 | 12/2010 | Wang et al. | |
| 7,862,563 B1 | 1/2011 | Cosman et al. | |
| 7,867,227 B2 | 1/2011 | Slater | |
| 7,879,029 B2 | 2/2011 | Jimenez | |
| 7,918,851 B2 | 4/2011 | Webster, Jr. et al. | |
| 7,925,341 B2 | 4/2011 | Fuimaono | |
| 7,927,328 B2 | 4/2011 | Orszulak et al. | |
| 7,933,660 B2 | 4/2011 | Carr | |

(56) References Cited

U.S. PATENT DOCUMENTS

| | | |
|---|---|---|
| 7,955,369 B2 | 6/2011 | Thompson et al. |
| 7,959,628 B2 | 6/2011 | Schaer et al. |
| 7,967,817 B2 | 6/2011 | Anderson et al. |
| 7,976,537 B2 | 7/2011 | Lieber et al. |
| 7,989,741 B2 | 8/2011 | Carr |
| 7,998,140 B2 | 8/2011 | McClurken et al. |
| 7,998,141 B2 | 8/2011 | Wittkampf et al. |
| 8,012,150 B2 | 9/2011 | Wham et al. |
| 8,034,052 B2 | 10/2011 | Podhajsky |
| 8,038,670 B2 | 10/2011 | McClurken |
| 8,048,070 B2 | 11/2011 | O'Brien et al. |
| 8,052,684 B2 | 11/2011 | Wang et al. |
| 8,062,228 B2 | 11/2011 | Carr |
| 8,083,736 B2 | 12/2011 | McClurken et al. |
| 8,100,895 B2 | 1/2012 | Panos et al. |
| 8,104,956 B2 | 1/2012 | Blaha |
| 8,118,809 B2 | 2/2012 | Paul et al. |
| 8,123,745 B2 | 2/2012 | Beeckler et al. |
| 8,133,220 B2 | 3/2012 | Lee et al. |
| 8,152,801 B2 | 4/2012 | Goldberg et al. |
| 8,157,796 B2 | 4/2012 | Collins et al. |
| 8,160,693 B2 | 4/2012 | Fuimaono |
| 8,206,380 B2 * | 6/2012 | Lenihan et al. .............. 606/33 |
| 8,211,099 B2 | 7/2012 | Buysse et al. |
| 8,216,216 B2 | 7/2012 | Warnking et al. |
| 8,256,428 B2 | 9/2012 | Hindricks et al. |
| 8,262,652 B2 | 9/2012 | Podhajsky |
| 8,262,653 B2 | 9/2012 | Plaza |
| 8,265,747 B2 | 9/2012 | Rittman, III et al. |
| 8,267,929 B2 | 9/2012 | Wham et al. |
| 8,267,932 B2 | 9/2012 | Baxter et al. |
| 8,287,532 B2 | 10/2012 | Carroll et al. |
| 8,287,533 B2 | 10/2012 | Wittkampf et al. |
| 8,298,223 B2 | 10/2012 | Wham et al. |
| 8,298,227 B2 | 10/2012 | Leo et al. |
| 8,303,172 B2 | 11/2012 | Zei et al. |
| 8,303,580 B2 | 11/2012 | Wham et al. |
| 8,333,759 B2 | 12/2012 | Podhajsky |
| 8,333,762 B2 | 12/2012 | Mest et al. |
| 8,359,092 B2 | 1/2013 | Hayam et al. |
| 8,374,670 B2 | 2/2013 | Selkee |
| 8,398,623 B2 | 3/2013 | Warnking et al. |
| 8,409,192 B2 | 4/2013 | Asirvatham et al. |
| 8,414,570 B2 | 4/2013 | Turner et al. |
| 8,414,579 B2 | 4/2013 | Kim et al. |
| 8,440,949 B2 | 5/2013 | Carr |
| 8,449,539 B2 | 5/2013 | Wang et al. |
| 8,473,023 B2 | 6/2013 | Worley et al. |
| 8,475,448 B2 | 7/2013 | Sharareh et al. |
| 8,475,450 B2 | 7/2013 | Govari et al. |
| 8,480,666 B2 | 7/2013 | Buysse et al. |
| 8,515,554 B2 | 8/2013 | Carr |
| 8,517,999 B2 | 8/2013 | Pappone et al. |
| 8,545,409 B2 | 10/2013 | Sliwa et al. |
| 8,574,166 B2 | 11/2013 | Carr |
| 8,731,684 B2 | 5/2014 | Carr et al. |
| 2002/0128636 A1 | 9/2002 | Chin et al. |
| 2002/0169444 A1 | 11/2002 | Mest et al. |
| 2003/0078573 A1 | 4/2003 | Truckai et al. |
| 2004/0054272 A1 | 3/2004 | Messing |
| 2004/0092806 A1 | 5/2004 | Sagon et al. |
| 2005/0015082 A1 | 1/2005 | O'Sullivan et al. |
| 2005/0033221 A1 | 2/2005 | Fuimaono |
| 2005/0228370 A1 | 10/2005 | Sterzer et al. |
| 2006/0184221 A1 | 8/2006 | Stewart et al. |
| 2007/0032788 A1 | 2/2007 | Edwards et al. |
| 2007/0055326 A1 | 3/2007 | Farley et al. |
| 2007/0055328 A1 | 3/2007 | Mayse et al. |
| 2007/0066968 A1 | 3/2007 | Rahn |
| 2007/0066972 A1 | 3/2007 | Ormsby et al. |
| 2007/0156114 A1 | 7/2007 | Worley et al. |
| 2007/0244476 A1 | 10/2007 | Kochamba et al. |
| 2007/0244534 A1 | 10/2007 | Kochamba et al. |
| 2008/0033300 A1 | 2/2008 | Hoang et al. |
| 2008/0082091 A1 | 4/2008 | Rubtsov et al. |
| 2008/0177205 A1 | 7/2008 | Rama et al. |
| 2008/0249463 A1 | 10/2008 | Pappone et al. |
| 2009/0005768 A1 | 1/2009 | Sharareh et al. |
| 2009/0069808 A1 | 3/2009 | Pike, Jr. et al. |
| 2009/0076409 A1 | 3/2009 | Wu et al. |
| 2009/0099560 A1 | 4/2009 | Rioux et al. |
| 2009/0118613 A1 | 5/2009 | Krugman et al. |
| 2009/0177193 A1 | 7/2009 | Wang et al. |
| 2009/0221999 A1 | 9/2009 | Shahidi |
| 2009/0248006 A1 | 10/2009 | Paulus et al. |
| 2009/0254083 A1 | 10/2009 | Wallace et al. |
| 2009/0287201 A1 | 11/2009 | Lalonde et al. |
| 2009/0312754 A1 | 12/2009 | Lenihan et al. |
| 2009/0312756 A1 | 12/2009 | Schlesinger et al. |
| 2010/0016848 A1 | 1/2010 | Desai |
| 2010/0030209 A1 | 2/2010 | Govari et al. |
| 2010/0057072 A1 | 3/2010 | Roman et al. |
| 2010/0057073 A1 | 3/2010 | Roman et al. |
| 2010/0057074 A1 | 3/2010 | Roman et al. |
| 2010/0057080 A1 | 3/2010 | West et al. |
| 2010/0076424 A1 | 3/2010 | Carr |
| 2010/0094271 A1 | 4/2010 | Ward et al. |
| 2010/0114087 A1 | 5/2010 | Edwards et al. |
| 2010/0137837 A1 | 6/2010 | Govari et al. |
| 2010/0137857 A1 | 6/2010 | Shroff et al. |
| 2010/0168570 A1 | 7/2010 | Sliwa et al. |
| 2010/0168571 A1 | 7/2010 | Savery et al. |
| 2010/0174280 A1 | 7/2010 | Grimaldi |
| 2010/0185191 A1 | 7/2010 | Carr et al. |
| 2010/0204691 A1 | 8/2010 | Bencini |
| 2010/0211070 A1 | 8/2010 | Subramaniam et al. |
| 2010/0217255 A1 | 8/2010 | Greeley et al. |
| 2010/0222859 A1 | 9/2010 | Govari et al. |
| 2010/0286684 A1 | 11/2010 | Hata et al. |
| 2011/0009857 A1 | 1/2011 | Subramaniam et al. |
| 2011/0022041 A1 | 1/2011 | Ingle et al. |
| 2011/0066147 A1 | 3/2011 | He et al. |
| 2011/0077498 A1 | 3/2011 | McDaniel |
| 2011/0118726 A1 | 5/2011 | de la Rama et al. |
| 2011/0144639 A1 | 6/2011 | Govari |
| 2011/0152853 A1 | 6/2011 | Manley et al. |
| 2011/0160726 A1 | 6/2011 | Ingle |
| 2011/0213356 A1 | 9/2011 | Wright et al. |
| 2011/0224664 A1 | 9/2011 | Bar-Tal et al. |
| 2011/0264011 A1 | 10/2011 | Wu et al. |
| 2011/0264089 A1 | 10/2011 | Zirkle et al. |
| 2011/0270244 A1 | 11/2011 | Clark et al. |
| 2011/0270246 A1 | 11/2011 | Clark et al. |
| 2011/0282342 A1 | 11/2011 | Leo et al. |
| 2011/0288544 A1 | 11/2011 | Verin et al. |
| 2011/0295247 A1 | 12/2011 | Schlesinger et al. |
| 2011/0319748 A1 | 12/2011 | Bronskill et al. |
| 2012/0035603 A1 | 2/2012 | Lenihan |
| 2012/0078138 A1 | 3/2012 | Leo et al. |
| 2012/0089123 A1 | 4/2012 | Organ et al. |
| 2012/0123411 A1 | 5/2012 | Ibrahim et al. |
| 2012/0130364 A1 | 5/2012 | Besch et al. |
| 2012/0136346 A1 | 5/2012 | Condie et al. |
| 2012/0143097 A1 | 6/2012 | Pike, Jr. |
| 2012/0150170 A1 | 6/2012 | Buysse et al. |
| 2012/0157890 A1 | 6/2012 | Govari et al. |
| 2012/0157990 A1 | 6/2012 | Christian |
| 2012/0165809 A1 | 6/2012 | Christian et al. |
| 2012/0172859 A1 | 7/2012 | Condie et al. |
| 2012/0179068 A1 | 7/2012 | Leo et al. |
| 2012/0239019 A1 | 9/2012 | Asconeguy |
| 2012/0245577 A1 | 9/2012 | Mihalik et al. |
| 2012/0265190 A1 | 10/2012 | Curley et al. |
| 2012/0271306 A1 | 10/2012 | Buysse et al. |
| 2012/0277737 A1 | 11/2012 | Curley |
| 2012/0283534 A1 | 11/2012 | Carr et al. |
| 2012/0283722 A1 | 11/2012 | Asconeguy |
| 2012/0302877 A1 | 11/2012 | Harks et al. |
| 2013/0006238 A1 | 1/2013 | Ditter et al. |
| 2013/0030385 A1 | 1/2013 | Schultz et al. |
| 2013/0030426 A1 | 1/2013 | Gallardo et al. |
| 2013/0030427 A1 | 1/2013 | Betts et al. |
| 2013/0060245 A1 | 3/2013 | Grunewald et al. |
| 2013/0079768 A1 | 3/2013 | De Luca et al. |

(56) References Cited

U.S. PATENT DOCUMENTS

| | | |
|---|---|---|
| 2013/0123775 A1 | 5/2013 | Grunewald et al. |
| 2013/0158536 A1 | 6/2013 | Bloom |
| 2013/0172873 A1 | 7/2013 | Govari et al. |
| 2013/0190747 A1 | 7/2013 | Koblish et al. |
| 2013/0197504 A1 | 8/2013 | Cronin et al. |
| 2013/0197507 A1 | 8/2013 | Kim et al. |
| 2013/0204240 A1 | 8/2013 | McCarthy et al. |
| 2013/0237977 A1 | 9/2013 | McCarthy et al. |
| 2013/0237979 A1 | 9/2013 | Shikhman et al. |
| 2013/0253504 A1 | 9/2013 | Fang |
| 2013/0253505 A1 | 9/2013 | Schultz |
| 2013/0281851 A1 | 10/2013 | Carr et al. |
| 2013/0324993 A1 | 12/2013 | McCarthy et al. |
| 2014/0012132 A1 | 1/2014 | Carr et al. |
| 2014/0018697 A1 | 1/2014 | Allison |

FOREIGN PATENT DOCUMENTS

| | | |
|---|---|---|
| EP | 2008602 A1 | 12/2008 |
| EP | 2294490 A1 | 3/2011 |
| WO | WO 99/03535 | 1/1999 |
| WO | WO 99/44523 A1 | 9/1999 |
| WO | WO 03/047446 A1 | 6/2003 |
| WO | WO 2004/073505 A2 | 9/2004 |
| WO | WO 2004/084748 | 10/2004 |
| WO | WO 2004/107974 A2 | 12/2004 |
| WO | WO 2006/074571 A1 | 7/2006 |
| WO | WO 2008/002517 A1 | 1/2008 |
| WO | WO 2010/090701 A1 | 8/2010 |
| WO | WO 2013/009977 A1 | 1/2013 |
| WO | WO 2013/019544 A1 | 2/2013 |
| WO | WO 2013/034629 A1 | 3/2013 |
| WO | WO 2013/119620 A1 | 8/2013 |
| WO | WO 2013/123020 A1 | 8/2013 |
| WO | WO 2013/138262 A1 | 9/2013 |

OTHER PUBLICATIONS

Carr, "Thermography: Radiometric sensing in medicine," New Frontiers in Medical Device Technology, Edited by Rosen et al., pp. 311-342, 1995.

El-Sharkawy et al., "Absolute temperature monitoring using RF radiometry in the MRI scanner," IEEE Trans Circuits Syst I Regul Pap. 53(11): 2396-2404, Nov. 2006.

Jacobsen et al., "Dual-mode antenna design for microwave heating and noninvasive thermometry of superficial tissue disease," IEEE Transactions on Biomedical Engineering 47(11): 1500-1509, Nov. 2000.

Stevenson, "Irrigated RF ablation: Power titration and fluid management for optimal safety and efficacy," Biosense Webster, Inc., 4 pages 2005.

Yazdandoost et al., "Theoretical study of the power distributions for interstitial microwave hyperthermia," Proceedings of the 2002 WSEAS International Conferences, Cadiz, Spain, pp. 1021-1025, Jun. 12-16, 2002.

Chierchia et al., "An Initial Clinical Experience with a Novel Microwave Radiometry Sensing Technology used in Irrigated RF Ablation for Flutter" (date Jan. 1, 2011).

Ikeda et al., "Microwave Volumetric Temperature Sensor Improves Control of Radiofrequency Lesion Formation and Steam Pop," Presentation Abstract, May 2012.

Ikeda et al., "Novel Irrigated Radiofrequency Ablation Catheter With Microwave Volumetric Temperature Sensor Predicts Lesion Size and Incidence of Steam Pop in Canine Beating Heart," Presentation Abstract, May 2012.

Koruth et al., "Tissue Temperature Sensing During Irrigated Radiofrequency Ablation: A Novel Strategy to Predict Steam Pops," Presentation Abstract, May 2012.

Koruth et al., "Occurrence of Steam Pops During Irrigated RF Ablation: Novel Insights from Microwave Radiometry," Journal of Interventional Cardiac Electrophysiology, vol. 24, Issue 11, pp. 1271-1277, Nov. 2013.

Lantis et al, "Microwave Applications in Clinical Medicine," Surgical Endoscopy, vol. 12, Issue 2, pp. 170-176, Feb. 1998.

Vandekerckhove et al., "Flutter Ablation With an Irrigated Catheter Using Microwave Radiometry Sensing Technology: first report in men" (date Jan. 1, 2011).

Wang et al., "Microwave Radiometric Thermometry and its Potential Applicability to Ablative Therapy," Journal of Interventional Cardiac Electrophysiology, vol. 4, pp. 295-300, Apr. 2000.

Wang et al., "Tissue Dielectric Measurement Using an Interstitial Dipole Antenna," IEEE Trans Biomed. Eng., vol. 59, Issue 1, Jan. 2012.

* cited by examiner

METHODS OF DETERMINING TISSUE TEMPERATURES IN ENERGY DELIVERY PROCEDURES

CROSS-REFERENCE TO RELATED APPLICATIONS

This application is a continuation application of U.S. patent application Ser. No. 13/368,112, filed on Feb. 7, 2012, the entirety of which is hereby incorporated by reference herein.

FIELD

This application generally relates to systems and methods for measuring temperature during tissue ablation.

BACKGROUND

Tissue ablation may be used to treat a variety of clinical disorders. For example, tissue ablation may be used to treat cardiac arrhythmias by destroying aberrant pathways that would otherwise conduct abnormal electrical signals to the heart muscle. Several ablation techniques have been developed, including cryoablation, microwave ablation, radio frequency (RF) ablation, and high frequency ultrasound ablation. For cardiac applications, such techniques are typically performed by a clinician who introduces a catheter having an ablative tip to the endocardium via the venous vasculature, positions the ablative tip adjacent to what the clinician believes to be an appropriate region of the endocardium based on tactile feedback, mapping electrocardiogram (ECG) signals, anatomy, and/or fluoroscopic imaging, actuates flow of an irrigant to cool the surface of the selected region, and then actuates the ablative tip for a period of time believed sufficient to destroy tissue in the selected region.

Although commercially available ablative tips may include thermocouples for providing temperature feedback via a digital display, such thermocouples typically do not provide meaningful temperature feedback during irrigated ablation. For example, the thermocouple only measures surface temperature, whereas the heating or cooling of the tissue that results in tissue ablation may occur at some depth below the tissue surface. Moreover, for procedures in which the surface of the tissue is cooled with an irrigant, the thermocouple will measure the temperature of the irrigant, thus further obscuring any useful information about the temperature of the tissue, particularly at depth. As such, the clinician has no useful feedback regarding the temperature of the tissue as it is being ablated or whether the time period of the ablation is sufficient.

Accordingly, it may only be revealed after the procedure is completed—for example, if the patient continues to experience cardiac arrhythmias—that the targeted aberrant pathway was not adequately interrupted. In such a circumstance, the clinician may not know whether the procedure failed because the incorrect region of tissue was ablated, because the ablative tip was not actuated for a sufficient period of time to destroy the aberrant pathway, because the ablative tip was not touching or insufficiently touching the tissue, because the power of the ablative energy was insufficient, or some combination of the above. Upon repeating the ablation procedure so as to again attempt to treat the arrhythmia, the clinician may have as little feedback as during the first procedure, and thus potentially may again fail to destroy the aberrant pathway. Additionally, there may be some risk that the clinician would re-treat a previously ablated region of the endocardium and not only ablate the conduction pathway, but damage adjacent tissues.

In some circumstances, to avoid having to repeat the ablation procedure as such, the clinician may ablate a series of regions of the endocardium along which the aberrant pathway is believed to lie, so as to improve the chance of interrupting conduction along that pathway. However, there is again insufficient feedback to assist the clinician in determining whether any of those ablated regions are sufficiently destroyed.

U.S. Pat. No. 4,190,053 to Sterzer describes a hyperthermia treatment apparatus in which a microwave source is used to deposit energy in living tissue to effect hyperthermia. The apparatus includes a radiometer for measuring temperature at depth within the tissue, and includes a controller that feeds back a control signal from the radiometer, corresponding to the measured temperature, to control the application of energy from the microwave source. The apparatus alternates between delivering microwave energy from the microwave source and measuring the radiant energy with the radiometer to measure the temperature. As a consequence of this time division multiplexing of energy application and temperature measurement, temperature values reported by the radiometer are not simultaneous with energy delivery.

U.S. Pat. No. 7,769,469 to Carr et al. describes an integrated heating and sensing catheter apparatus for treating arrhythmias, tumors and like, having a diplexer that permits near simultaneous heating and temperature measurement. This patent too describes that temperature measured by the radiometer may be used to control the application of energy, e.g., to maintain a selected heating profile.

Despite the promise of precise temperature measurement sensitivity and control offered by the use of radiometry, there have been few successful commercial medical applications of this technology. One drawback of previously-known systems has been an inability to obtain highly reproducible results due to slight variations in the construction of the microwave antenna used in the radiometer, which can lead to significant differences in measured temperature from one catheter to another. Problems also have arisen with respect to orienting the radiometer antenna on the catheter to adequately capture the radiant energy emitted by the tissue, and with respect to shielding high frequency microwave components in the surgical environment so as to prevent interference between the radiometer components and other devices in the surgical field.

Acceptance of microwave-based hyperthermia treatments and temperature measurement techniques also has been impeded by the capital costs associated with implementing radiometric temperature control schemes. Radiofrequency ablation techniques have developed a substantial following in the medical community, even though such systems can have severe limitations, such as the inability to accurately measure tissue temperature at depth, e.g., where irrigation is employed. However, the widespread acceptance of RF ablation systems, extensive knowledge base of the medical community with such systems, and the significant cost required to changeover to, and train for, newer technologies has dramatically retarded the widespread adoption of radiometry.

In view of the foregoing, it would be desirable to provide apparatus and methods that permit radiometric measurement of temperature at depth in tissue, and permit use of such measurements to control the application of energy in a hyperthermia treatment.

It further would be desirable to provide apparatus and methods that employ microwave radiometer components that can be readily constructed and calibrated to provide a high degree of measurement reproducibility and reliability.

It also would be desirable to provide apparatus and methods that permit radiometric temperature measurement and control techniques to be introduced in a manner that is readily accessible to clinicians trained in the use of previously-known RF ablation catheters, with a minimum of retraining.

It still further would be desirable to provide apparatus and methods that permit radiometric temperature measurement and control techniques to be readily employed with previously-known RF electrosurgical generators, thereby reducing the capital costs needed to implement such new techniques.

SUMMARY

In view of the foregoing, it would be desirable to provide apparatus and methods for treating living tissue that employs a radiometer for temperature measurement and control. In accordance with one aspect of the invention, systems and methods are provided for radiometrically measuring temperature during RF ablation, i.e., calculating temperature based on signal(s) from a radiometer. Unlike standard thermocouple techniques used in existing commercial ablation systems, a radiometer may provide useful information about tissue temperature at depth—where the tissue ablation occurs—and thus provide feedback to the clinician about the extent of tissue damage as the clinician ablates a selected region of the heart muscle.

In one embodiment, the present invention comprises an interface module (system) that may be coupled to a previously-known commercially available ablation energy generator, e.g., an electrosurgical generator, thereby enabling radiometric techniques to be employed with reduced capital outlay. In this manner, the conventional electrosurgical generator can be used to supply ablative energy to an "integrated catheter tip" (ICT) that includes an ablative tip, a thermocouple, and a radiometer for detecting the volumetric temperature of tissue subjected to ablation. The interface module is configured to be coupled between the conventional electrosurgical generator and the ICT, and to coordinate signals therebetween. The interface module thereby provides the electrosurgical generator with the information required for operation, transmits ablative energy to the ICT under the control of the clinician, and displays via a temperature display the temperature at depth of tissue as it is being ablated, for use by the clinician. The displayed temperature may be calculated based on signal(s) measured by the radiometer using algorithms such as discussed further below.

In an exemplary embodiment, the interface module includes a first input/output (I/O) port that is configured to receive a digital radiometer signal and a digital thermocouple signal from the ICT, and a second I/O port that is configured to receive ablative energy from the electrosurgical generator. The interface module also includes a processor, a patient relay in communication with the processor and the first and second I/O ports, and a persistent computer-readable medium. The computer-readable medium stores operation parameters for the radiometer and the thermocouple, as well as instructions for the processor to use in coordinating operation of the ICT and the electrosurgical generator.

The computer-readable medium preferably stores instructions that cause the processor to execute the step of calculating a temperature adjacent to the ICT based on the digital radiometer signal, the digital thermocouple signal, and the operation parameters. This temperature is expected to provide significantly more accurate information about lesion quality and temperature at depth in the tissue than would a temperature based solely on a thermocouple readout. The computer-readable medium may further store instructions for causing the processor to cause the temperature display to display the calculated temperature, for example so that the clinician may control the time period for ablation responsive to the displayed temperature. The computer-readable medium may further store instructions for causing the processor to close the patient relay, such that the patient relay passes ablative energy received on the second I/O port, from the electrosurgical generator, to the first I/O port, to the ICT. Note that the instructions may cause the processor to maintain the patient relay in a normally closed state, and to open the patient relay upon detection of unsafe conditions.

DETAILED DESCRIPTION

Embodiments of the present invention provide systems and methods for radiometrically measuring temperature during ablation, in particular cardiac ablation. As noted above, commercially available systems for cardiac ablation may include thermocouples for measuring temperature, but such thermocouples may not adequately provide the clinician with information about tissue temperature. Thus, the clinician may need to make an "educated guess" about whether a given region of tissue has been sufficiently ablated to achieve the desired effect. By comparison, calculating a temperature based on signal(s) from a radiometer is expected to provide accurate information about the temperature of tissue at depth, even during an irrigated procedure. The present invention provides a "retrofit" solution that includes an interface module that works with existing, commercially available ablation energy generators, such as electrosurgical generators. In accordance with one aspect of the present invention, the interface module displays a tissue temperature based on signal(s) measured by a radiometer, that a clinician may use to perform ablation procedures with significantly better accuracy than can be achieved using only a thermocouple for temperature measurement.

First, high level overviews of the interface module and connections thereto are provided. Then, further detail on the internal components of the interface module, and exemplary methods of calculating radiometric temperature and controlling an ablation procedure based on same, are provided. Data obtained during experimental procedures also is presented. Lastly, further detail on components that may be used with the interface module is provided.

Figure 1A:
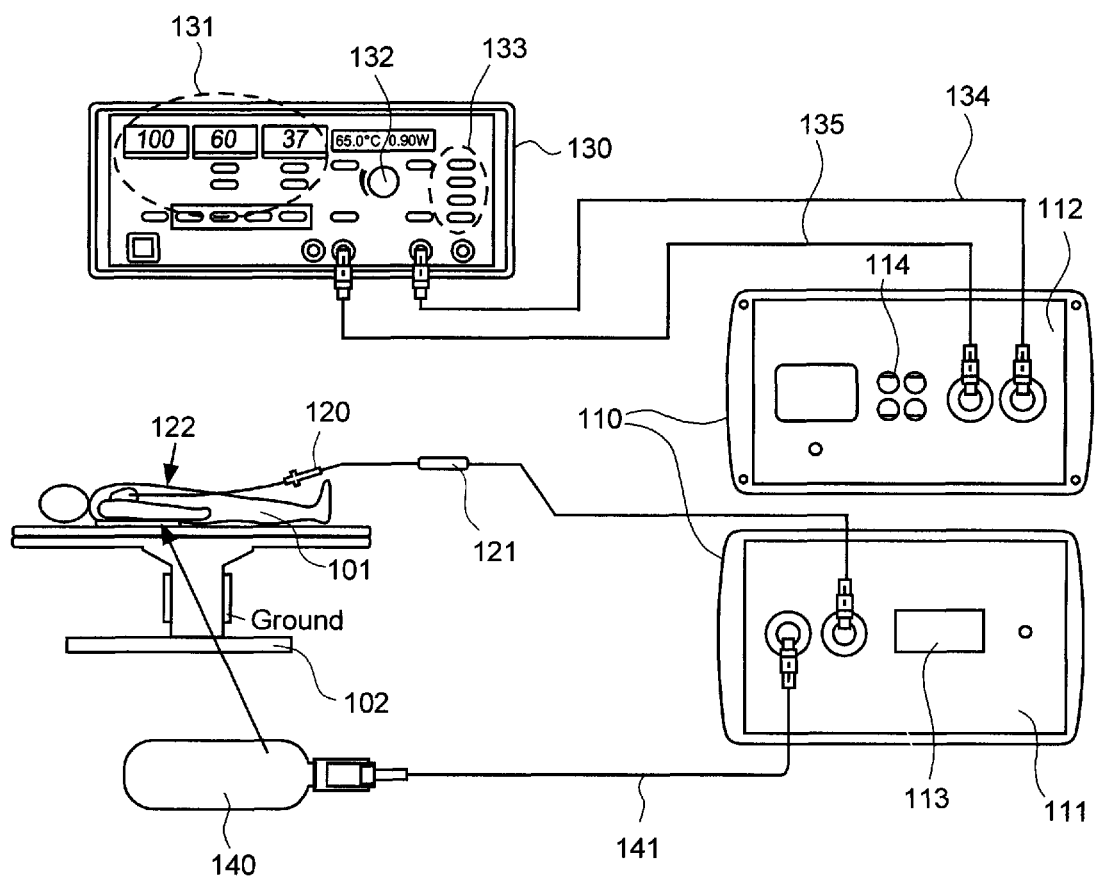
FIG. 1A is a schematic illustration of a first embodiment of an arrangement including an interface module according to one aspect of the present invention, including a display of the front and back panels of, and exemplary connections between, the interface module, a previously known ablation energy generator, e.g., electrosurgical generator, and an integrated catheter tip (ICT).

FIG. 1A illustrates plan views of front panel 111, back panel 112, and connections to and from exemplary interface module 110, constructed in accordance with the principles of the present invention. As illustrated, front panel 111 of interface module 110 may be connected to a catheter 120 that includes patient interface module (PIM) 121 and integrated catheter tip (ICT) 122. Catheter 120 optionally is steerable, or may be non-steerable and used in conjunction with a robotic positioning system or a third-party steerable sheath (not shown). ICT 122 is positioned by a clinician (optionally with mechanical assistance such as noted above), during a procedure, within subject 101 lying on grounded table 102. ICT 122 may include, among other things, an ablative tip, a thermocouple, and a radiometer for detecting the volumetric temperature of tissue subjected to ablation. The ICT 122 optionally includes one or more irrigation ports, which in one embodiment may be connected directly to a commercially available irrigant pump.

In embodiments in which the ablation energy is radiofrequency (RF) energy, the ablative tip may include an irrigated ablation electrode, such as described in greater detail below with reference to FIGS. 6A-6B. ICT 122 further may include one or more electrocardiogram (ECG) electrodes for use in monitoring electrical activity of the heart of subject 101. Interface module 110 receives signals from the thermocouple, radiometer, and optional ECG electrodes of ICT 122 via PIM 121. Interface module 110 provides to ICT 122, via PIM 121, power for the operation of the PIM and the sensors (thermocouple, radiometer, and ECG electrodes), and ablation energy to be applied to subject 101 via the ablative tip.

Back panel 112 of interface module 110 may be connected via connection cable 135 to a commercially available previously-known ablation energy generator 130, for example an electrosurgical generator 130, such as a Stockert EP-Shuttle 100 Generator (Stockert GmbH, Freiburg Germany) or Stockert 70 RF Generator (Biosense Webster, Diamond Bar, Calif.). In embodiments where the electrosurgical generator 130 is a Stockert EP-Shuttle or 70 RF Generator, generator 130 includes display device 131 for displaying temperature and the impedance and time associated with application of a dose of RF ablation energy; power control knob 132 for allowing a clinician to adjust the power of RF ablative energy delivered to subject 101; and start/stop/mode input for allowing a clinician to initiate or terminate the delivery of RF ablation energy. Start/stop/mode input also may be configured to control the mode of energy delivery, e.g., whether the energy is to be cut off after a given period of time.

Although generator 130 may be configured to display temperature on display device 131, that temperature is based on readings from a standard thermocouple. As noted above, however, that reported temperature may be inaccurate while irrigant and ablative energy are being applied to tissue. Interface module 110 provides to generator 130, via connection cable 135, a thermocouple signal for use in displaying such a temperature, and signals from the ECG electrodes; and provides via indifferent electrode cable 134 a pass-through connection to indifferent electrode 140. Interface module 110 receives from generator 130, via connection cable 135, RF ablation energy that module 110 controllably provides to ICT 122 for use in ablating tissue of subject 101.

As will be familiar to those skilled in the art, for a monopolar RF ablation procedure, a clinician may position an indifferent electrode (IE) on the back of subject 101 so as to provide a voltage differential that enables transmission of RF energy into the tissue of the subject. In the illustrated embodiment, the IE is connected to interface module 110 via first indifferent electrode cable 141. Interface module 110 passes through the IE signal to second indifferent electrode cable 134, which is connected to an indifferent electrode input port on electrosurgical generator 130. Alternatively, the IE may be connected directly to that port of the electrosurgical generator 130 via appropriate cabling (not shown).

It should be understood that electrosurgical generators other than the Stockert EP-Shuttle or 70 RF Generator suitably may be used, e.g., other makes or models of RF electrosurgical generators. Alternatively, generators that produce other types of ablation energy, such as microwave generators, cryosurgical sources, or high frequency ultrasound generators, may be used. Ablation energy generator 130 need not necessarily be commercially available, although as noted above it may be convenient to use one that is. It should also be appreciated that the connections described herein may be provided on any desired face or panel of interface module 110, and that the functionalities of different connectors and input/output (I/O) ports may be combined or otherwise suitably modified.

Front panel 111 of interface module 110 includes temperature display 113, e.g., a digital two or three-digit display device configured to display a temperature calculated by a processor internal to interface module 110, e.g., as described in greater detail below with reference to FIGS. 2A-2B and 3A. Other types of temperature displays, such multicolor liquid crystal displays (LCDs), alternatively may be used. Front panel 111 also includes connectors (not labeled) through which interface module 110 is connected to ICT 122 via PIM 121, and to the IE 140 via indifferent electrode cable 141.

Back panel 111 of interface module 110 includes connectors (not labeled) through which interface module 110 is connected to electrosurgical generator 130, via indifferent electrode cable 134 and connection cable 135. Back panel 112 of interface module 110 also includes data ports 114 configured to output one or more signals to a suitably programmed personal computer or other remote device, for example an EP monitoring/recording system such as the LABSYSTEM™ PRO EP Recording System (C.R. Bard, Inc., Lowell, Mass.). Such signals may, for example, include signals generated by the thermocouple, radiometer, and/or ECG electrodes of the ICT, the tissue temperature calculated by interface module 110, and the like.

Figure 1B:
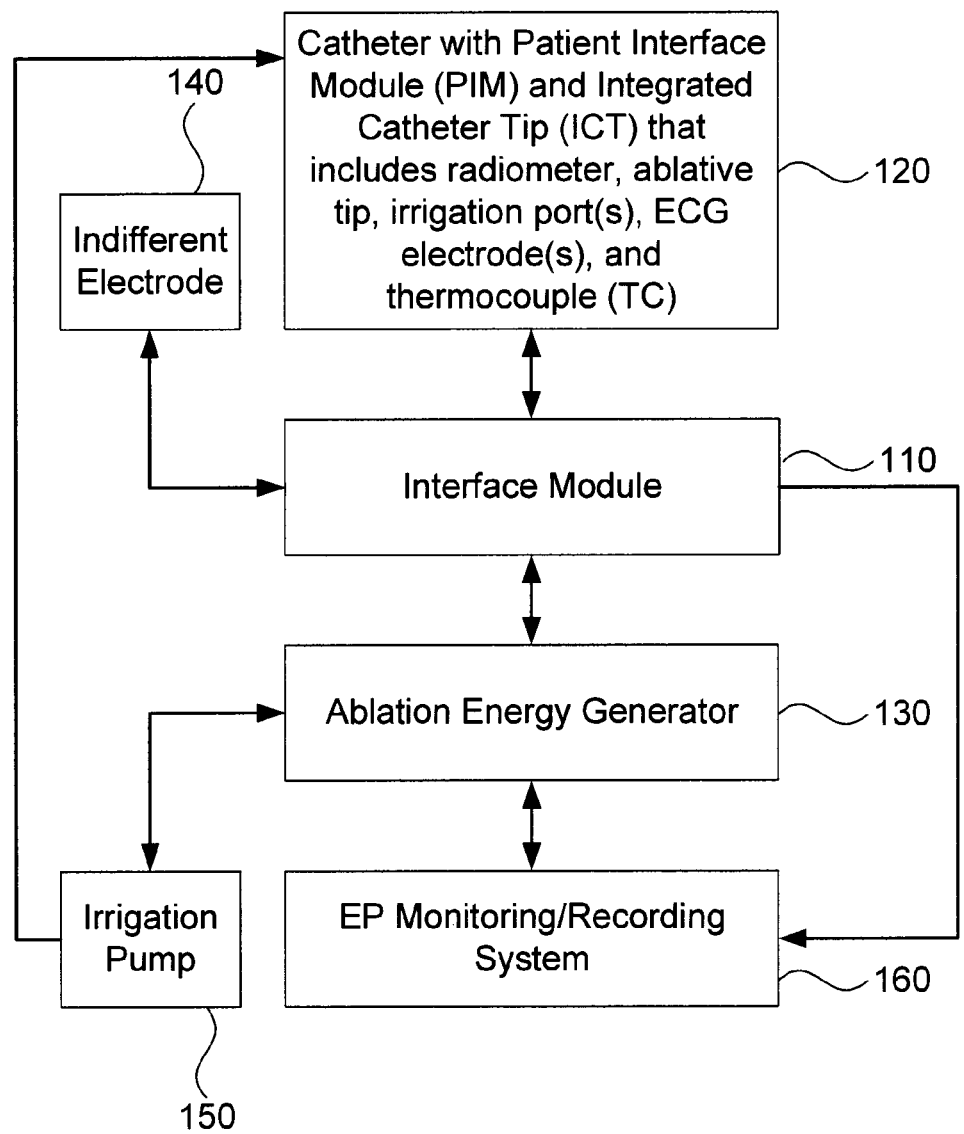
FIG. 1B is a schematic illustrating exemplary connections to and from the interface module of FIG. 1A, as well as connections among other components that may be used with the interface module.

Referring now to FIG. 1B, exemplary connections to and from the interface module of FIG. 1A, as well as connections among other components, are described. In FIG. 1B, interface module 110 is in operable communication with catheter 120 having a patient interface module (PIM) 121 and an integrated catheter tip (ICT) 122 that includes a radiometer, ablative tip, a thermocouple (TC), and optionally also includes ECG electrodes and/or irrigation ports(s). Interface module 110 is also in operable communication with electrosurgical generator 130 and indifferent electrode 140.

Electrosurgical generator 130 optionally is in operable communication with electrophysiology (EP) monitoring/recording system 160 via appropriate cabling. Alternatively, as illustrated in FIG. 1B, interface system 110 may be directly connected to EP monitoring/recording module 160 via appropriate cabling and data ports 114. EP monitoring/recording systems may include, for example, various monitors, processors, and the like that display pertinent information about an ablation procedure to a clinician, such as the subject's heart rate and blood pressure, the temperature recorded by the thermocouple on the catheter tip, the ablation power and time period over which it is applied, fluoroscopic images, and the like. EP monitoring/recording systems are commercially available, e.g., the MEDELEC™ Synergy T-EP—EMG/EP Monitoring System (CareFusion, San Diego, Calif.), or the LABSYSTEM™ PRO EP Recording System (C. R. Bard, Inc., Lowell, Mass.).

If the ICT 122 includes irrigation port(s), then one convenient means of providing irrigant to such ports is irrigation pump 140 associated with electrosurgical generator 130, which pump is in operable communication with the generator and in fluidic communication with the ICT. For example, the Stockert 70 RF Generator is designed for use with a CoolFlow™ Irrigation pump, also manufactured by Biosense Webster. Specifically, the Stockert 70 RF Generator and the CoolFlow™ pump may be connected to one another by a commercially available interface cable, so as to operate as an integrated system that works in substantially the same way as it would with a standard, commercially available catheter tip. For example, prior to positioning ICT 122 in the body, the clinician instructs the pump to provide a low flow rate of irrigant to the ICT, as it would to a standard catheter tip; the ICT is then positioned in the body. Then, when the clinician presses the "start" button on the face of generator 130, the generator may instruct pump 150 to provide a high flow rate of irrigant for a predetermined period (e.g., 5 seconds) before providing RF ablation energy, again as it would for a standard catheter tip. After the RF ablation energy application is terminated, then pump 150 returns to a low flow rate after another predetermined period (e.g., 5 seconds). The pump remains at a low flow rate until the clinician removes the ICT 122 from the body and manually turns off the pump.

Figure 2A:
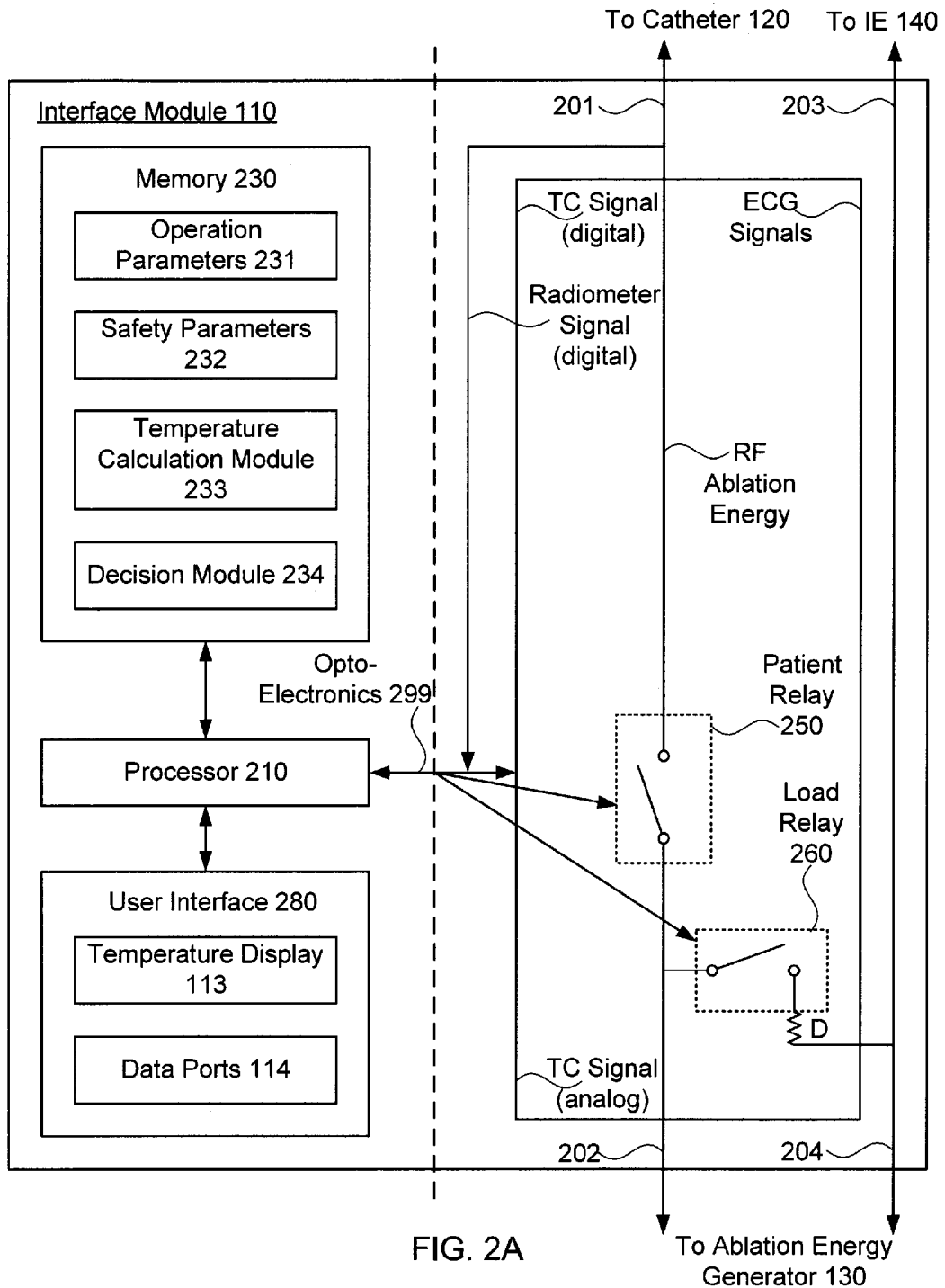
FIG. 2A is a schematic illustrating internal components of the interface module of FIGS. 1A-1B.
Figure 2B:
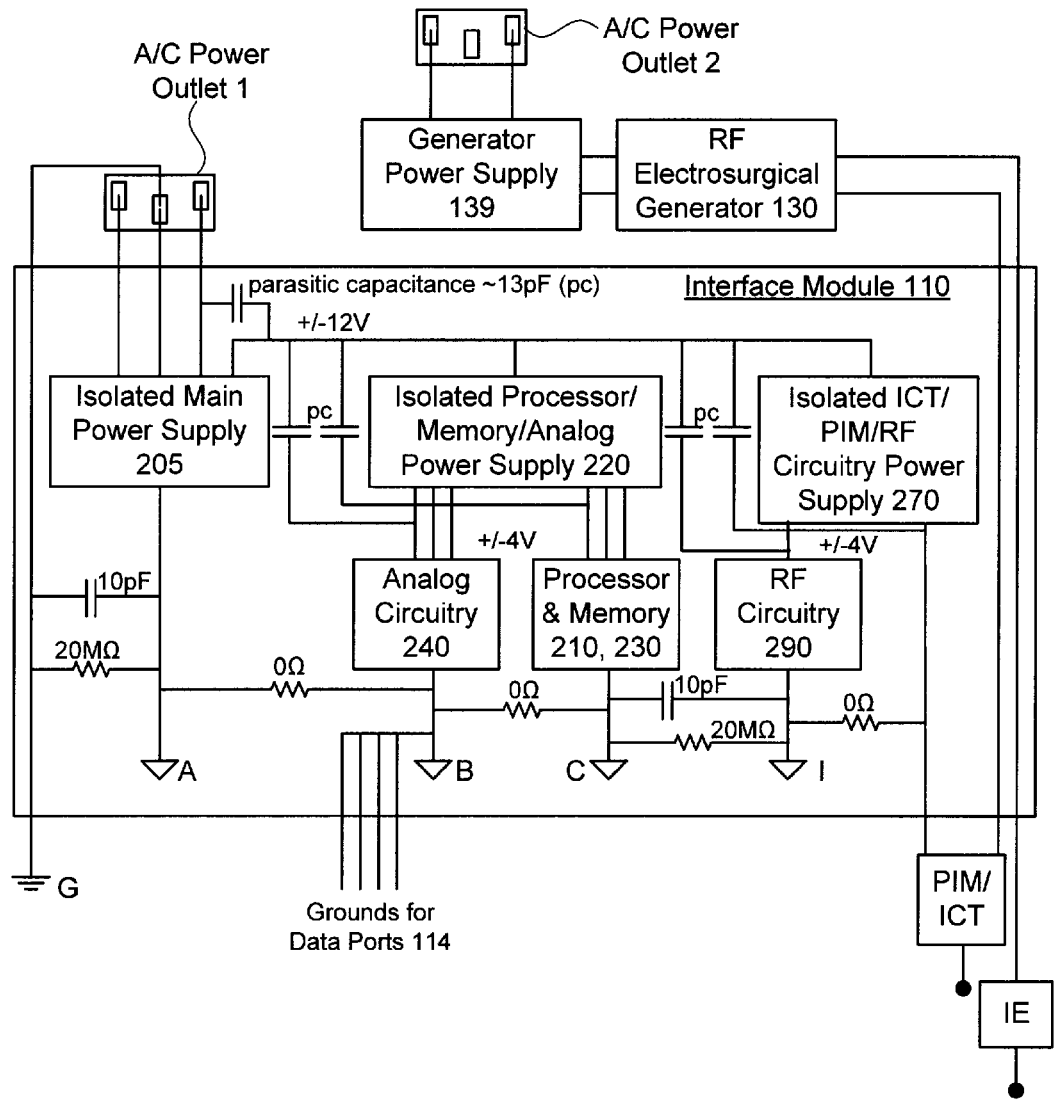
FIG. 2B schematically illustrates additional internal components of the interface module of FIG. 2A, as well as selected connections to and from the interface module.

Referring now to FIGS. 2A-2B, further details of internal components of interface module 110 of FIGS. 1A-1B are provided.

FIG. 2A schematically illustrates internal components of one embodiment of interface module 110. Interface module 110 includes first, second, third, and fourth ports 201-204 by which it communicates with external components. Specifically, first port 201 is an input/output (I/O) port configured to be connected to catheter 120 via PIM 121, as illustrated in FIG. 1A. Port 201 receives as input from catheter 120 digital radiometer and digital thermocouple (TC) signals, and optionally ECG signals, generated by ICT 122, and provides as output to catheter 120 RF ablation energy, as well as power for circuitry within the ICT 122 and the PIM 121. Second port 202 is also an I/O port, configured to be connected to electrosurgical generator 130 via connection cable 135 illustrated in FIG. 1A, and receives as input from generator 130 RF ablation energy, and provides as output to generator 130 a reconstituted analog thermocouple (TC) signal and raw ECG signal(s). Third port 203 is an input port configured to be connected to indifferent electrode (IE) 140 via indifferent electrode cable 134 illustrated in FIG. 1A, and fourth port 204 is an output port configured to be connected to generator 130 via indifferent electrode cable 141 illustrated in FIG. 1A. As shown in FIG. 2A, interface module 110 acts as a pass-through for the IE signal from IE 140 to generator 130, and simply receives IE signal on third port 203 and provides the IE signal to generator 130 on fourth port 204.

Interface module 110 also includes processor 210 coupled to non-volatile (persistent) computer-readable memory 230, user interface 280, load relay 260, and patient relay 250. Memory 230 stores programming that causes processor 210 to perform steps described further below with respect to FIGS. 3A-3C, thereby controlling the functionality of interface module 110. Memory 230 also stores parameters used by processor 210. For example, memory 230 may store a set of operation parameters 231 for the thermocouple and radiometer, as well as a temperature calculation module 233, that processor 210 uses to calculate the radiometric temperature based on the digital TC and radiometer signals received on first I/O port 201, as described in greater detail below with respect to FIG. 3B. The operation parameters 231 may be obtained through calibration, or may be fixed. Memory 230 also stores a set of safety parameters 232 that processor 210 uses to maintain safe conditions during an ablation procedure, as described further below with respect to FIG. 3C. Memory 230 further stores decision module 234 that processor 210 uses to control the opening and closing of patient relay 250 and load relay 260 based on its determinations of temperature and safety conditions, as described further below with reference to FIGS. 3A-3C. When closed, patient relay 250 passes ablative energy from the second I/O port 202 to the first I/O port 201. When closed, load relay 260 returns ablative energy to the IE 140 via dummy load D (resistor, e.g., of 120Ω resistance) and fourth I/O port 204.

As illustrated in FIG. 2A, interface module 110 further includes user interface 280 by which a user may receive information about the temperature adjacent ICT 122 as calculated by processor 210, as well as other potentially useful information. In the illustrated embodiment, user interface 280 includes digital temperature display 113, which displays the instantaneous temperature calculated by processor 210. In other embodiments (not shown), display 113 may be an LCD device that, in addition to displaying the instantaneous temperature calculated by processor 210, also graphically display changes in the temperature over time for use by the clinician during the ablation procedure. User interface 280 further may include data ports 114, which may be connected to a computer or EP monitoring/recording system by appropriate cabling as noted above, and which may output digital or analog signals being received or generated by interface module 110, e.g., radiometer signal(s), a thermocouple signal, and/or the temperature calculated by processor 210.

So as to inhibit potential degradations in the performance of processor 210, memory 230, or user interface 280 resulting from electrical contact with RF energy, interface module 110 may include opto-electronics 299 that communicate information to and from processor 210, but that substantially inhibit transmission of RF energy to processor 210, memory 230, or user interface 280. This isolation is designated by the dashed line in FIG. 2A. For example, opto-electronics 299 may include circuitry that is in operable communication with first I/O port 201 so as to receive the digital TC and radiometer signals from first I/O port 201, and that converts such digital signals into optical digital signals. Opto-electronics 299 also may include an optical transmitter in operable communication with such circuitry, that transmits those optical digital signals to processor 210 through free space. Opto-electronics 299 further may include an optical receiver in operable communication with processor 210, that receives such optical digital signals, and circuitry that converts the optical digital signals into digital signals for use by processor 210. The opto-electronic circuitry in communication with the processor also may be in operable communication with a second optical transmitter, and may receive signals from processor 210 to be transmitted across free space to an optical receiver in communication with the circuitry that receives and processes the digital TC and radiometer signals. For example, processor 210 may transmit to such circuitry, via an optical signal, a signal that causes the circuitry to generate an analog version of the TC signal and to provide that analog signal to the second I/O port. Because opto-electronic circuitry, transmitters, and receivers are known in the art, its specific components are not illustrated in FIG. 2A.

With respect to FIG. 2B, additional internal components of interface module 110 of FIG. 2A are described, as well as selected connections to and from the interface module. FIG. 2B is an exemplary schematic for a grounding and power supply scheme suitable for using interface module 110 with an RF electrosurgical generator, e.g., a Stockert EP-Shuttle or 70 RF Generator. Other grounding and power supply schemes suitably may be used with other types, makes, or models of electrosurgical generators, as will be appreciated by those skilled in the art.

As illustrated in FIG. 2B, interface module 110 includes isolated main power supply 205 that may be connected to standard three-prong A/C power outlet 1, which is grounded to mains ground G. Interface module 110 also includes several internal grounds, designated A, B, C, and I. Internal ground A is coupled to the external mains ground G via a relatively small capacitance capacitor (e.g., a 10 pF capacitor) and a relatively high resistance resistor (e.g., a 20 MΩ resistor) that substantially prevents internal ground A from floating. Internal ground B is coupled to internal ground A via a low resistance pathway (e.g., a pathway or resistor(s) providing less than 1000Ω resistance, e.g., about 0Ω resistance). Similarly, internal ground C is coupled to internal ground B via another low resistance pathway. Internal ground I is an isolated ground that is coupled to internal ground C via a relatively small capacitance capacitor (e.g., a 10 pF capacitor) and a relatively high resistance resistor (e.g., a 20 MΩ resistor) that substantially prevents isolated ground I from floating.

Isolated main power supply 205 is coupled to internal ground A via a low resistance pathway. Isolated main power supply 205 is also coupled to, and provides power (e.g., ±12V) to, one or more internal isolated power supplies that in turn provide power to components internal to interface module 110. Such components include, but are not limited to components illustrated in FIG. 2A. For example, interface module 110 may include one or more isolated power supplies 220 that provide power (e.g., ±4V) to processor 210, memory 230, and analog circuitry 240. Analog circuitry 240 may include components of user interface 280, including temperature display 113 and circuitry that appropriately prepares signals for output on data ports 114. Data ports 114, as well as analog circuitry 240, are coupled to internal ground B via low resistance pathways, while processor and memory 210, 230 are coupled to internal ground C via low resistance pathways. Interface module also may include one or more isolated power supplies 270 that provide power (e.g., ±4V) to ICT 122, PIM 121, and RF circuitry 290.

RF circuitry 290 may include patient and load relays 250, 260, as well as circuitry that receives the radiometer and thermocouple signals and provides such signals to the processor via optoelectronic coupling, and circuitry that generates a clock signal to be provided to the ICT as described further below with reference to FIG. 5B. RF circuitry 290, ICT 122, and PIM 121 are coupled to isolated internal ground I via low resistance pathways.

As shown in FIG. 2B, power supply 139 of RF electrosurgical generator 130, which may be external to generator 130 as in FIG. 2B or may be internal to generator 130, is connected to standard two- or three-prong A/C power outlet 2. However, generator power supply 139 is not connected to the ground of the outlet, and thus not connected to the mains ground G, as is the isolated main power supply. Instead, generator power supply 139 and RF electrosurgical generator 130 are grounded to internal isolated ground I of interface module 110 via low resistance pathways between generator 130 and PIM 121 and ICT 122, and low resistance pathways between PIM 121 and ICT 122 and internal isolated ground I. As such, RF circuitry 290, PIM 121, IE 140, and generator 130 are all "grounded" to an internal isolated ground I that has essentially the same potential as does ICT 122. Thus, when RF energy is applied to ICT 122 from generator 130 through interface module 110, the ground of RF circuitry 290, PIM 121, ICT 122, IE 140, and generator 130 all essentially float with the RF energy amplitude, which may be a sine wave of 50-100V at 500 kHz.

As further illustrated in FIG. 2B, the ±12V of power that isolated main power supply 205 provides to isolated processor/memory/analog power supply 220 and to isolated ICT/RF power supply 270 may be coupled by parasitic capacitance (pc, approximately 13 pF) to A/C power outlet 1, as may be the ±4V of power that such power supplies provide to their respective components. Such parasitic coupling will be familiar to those skilled in the art. Note also that the particular resistances, capacitances, and voltages described with reference to FIG. 2B are purely exemplary and may be suitably varied as appropriate to different configurations.

Figure 3A:
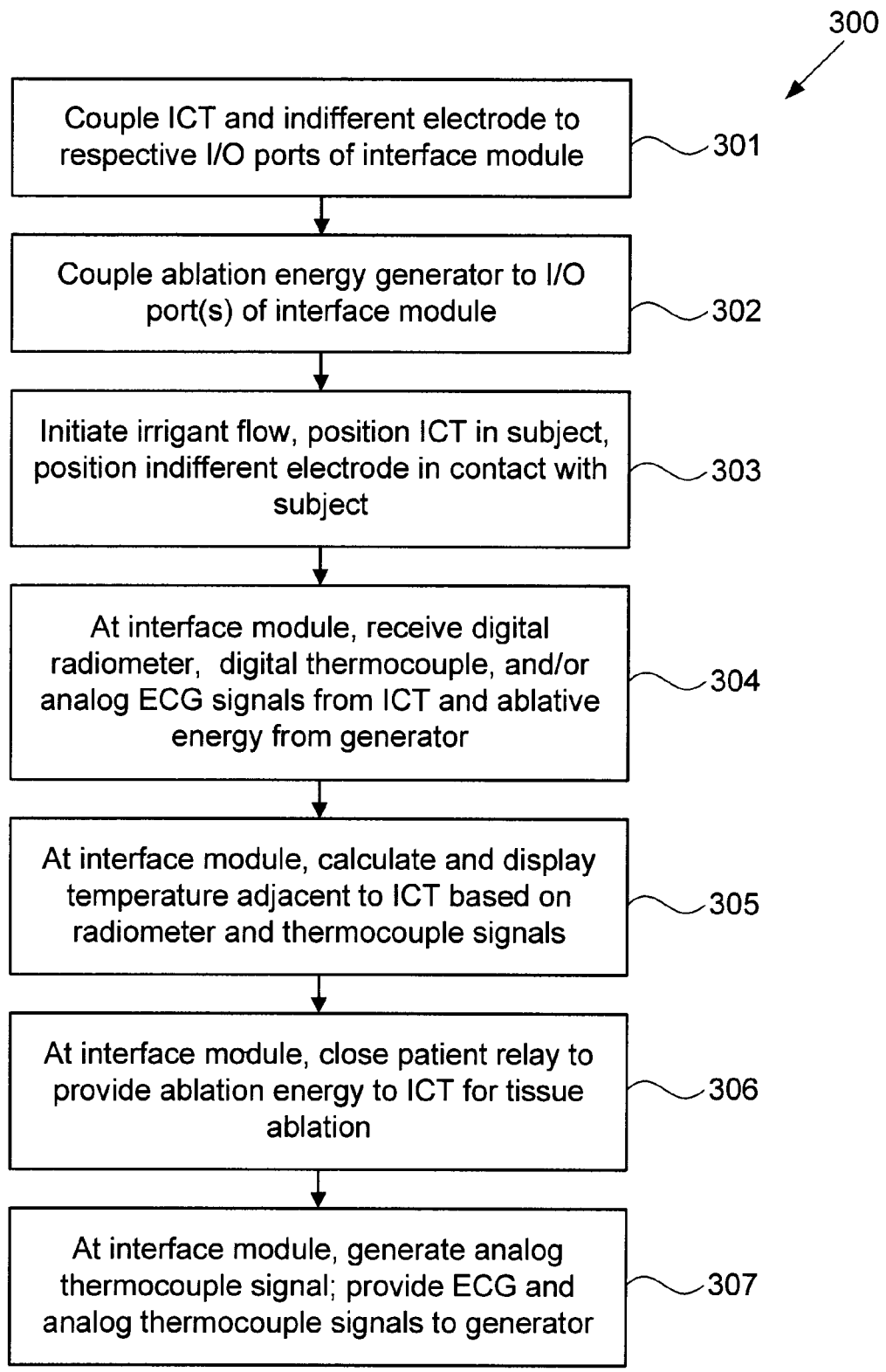
FIG. 3A illustrates steps in a method of using the interface module of FIGS. 1A-2B during tissue ablation.

Referring now to FIG. 3A, method 300 of using interface module 110 of FIGS. 1A-2B during a tissue ablation procedure is described. The clinician couples the integrated catheter tip (ICT) and indifferent electrode (IE) to respective I/O ports of the interface module (step 301). For example, as shown in FIG. 1A, ICT 122 may be coupled to a first connector on front panel 111 of interface module 110 via patient interface module (PIM) 121, and IE 140 may be coupled to a third connector on front panel 111 via indifferent electrode cable 141. The first connector is in operable communication with first I/O port 201 (see FIG. 2A) and the third connector is in operable communication with third I/O port 203 (see FIG. 2A).

In FIG. 3A, the clinician may couple the electrosurgical generator to I/O port(s) of the interface module (step 302). For example, as illustrated in FIG. 1A, electrosurgical generator 130 may be coupled to a second connector on back panel 112 of interface module 110 via connection cable 135, and also may be coupled to a fourth connector on back panel 112 via indifferent electrode cable 134. The second connector is in operable communication with second I/O port 202 (see FIG. 2A), and the fourth connector is in operable communication with fourth I/O port 204 (see FIG. 2A).

In FIG. 3A, the clinician initiates flow of irrigant, positions the ICT within the subject, e.g., in the subject's heart, and positions the IE in contact with the subject, e.g., on the subject's back (step 303). Those skilled in the art will be familiar with methods of appropriately positioning catheter tips relative to the heart of a subject, for example via the venous vasculature.

The interface module receives digital radiometer, digital thermocouple, and/or analog ECG signals from the ICT, and receives ablation energy from the generator (step 304), for example using the connections, ports, and pathways described above with references to FIGS. 1A-2B. Preferably, the generator may provide such ablation energy to the interface module responsive to the clinician pressing "start" using inputs 133 on the front face of generator 130 (see FIG. 1A).

The interface module calculates and displays the temperature adjacent to the ICT, based on the radiometer and thermocouple signals (step 305). This calculation may be performed, for example, by processor 210 based on instructions in temperature calculation module 233 stored in memory 230 (see FIG. 2A). Exemplary methods of performing such a calculation are described in greater detail below with respect to FIG. 3B.

In method 300, the interface module also closes the patient relay so as to provide ablation energy to the ICT for use in tissue ablation (step 306). For example, processor 210 may maintain patient relay 250 illustrated in FIG. 2A in a normally closed state during operation, such that ablation energy flows from electrosurgical generator 130 to ICT 122 through interface module 110 without delay upon the clinician's actuation of the generator, and may open patient relay 250 only upon detection of unsafe conditions such as described below with respect to FIG. 3C. In an alternative embodiment, processor 210 may maintain patient relay 250 in a normally open state during operation, and may determine based on instructions in decision module 234 and on the temperature calculated in step 305 that it is safe to proceed with tissue ablation, and then close patient relay so as to pass ablation energy to the ICT. In either case, after a time period defined using input 133 on the front face of generator 130, the supply of ablation energy ceases or the clinician manually turns off the supply of ablation energy.

The interface module also generates an analog version of the thermocouple signal, and provides the ECG and analog thermocouple signals to the generator (step 307). Preferably, step 307 is performed continuously by the interface module throughout steps 330 through 306, rather than just at the end of the ablation procedure. For example, as will be familiar to those skilled in the art, the Stockert EP-Shuttle or 70 RF Generator may "expect" certain signals to function properly, e.g., those signals that the generator would receive during a standard ablation procedure that did not include use of interface module 110. The Stockert EP-Shuttle or 70 RF generator requires as input an analog thermocouple signal, and optionally may accept analog ECG signal(s). The interface module 110 thus may pass through the ECG signal(s) generated by the ICT to the Stockert EP-shuttle or 70 RF generator via second I/O port 202. However, as described above with reference to FIGS. 2A and 3A, interface module 110 receives a digital thermocouple signal from ICT 122. In its standard configuration, the Stockert EP-Shuttle or 70 RF generator is not configured to receive or interpret a digital thermocouple signal. As such, interface module 110 includes the functionality of reconstituting an analog version of the thermocouple signal, for example using processor 210 and opto-electronics 299, and providing that analog signal to generator 130 via second I/O port 202.

Figure 3B:
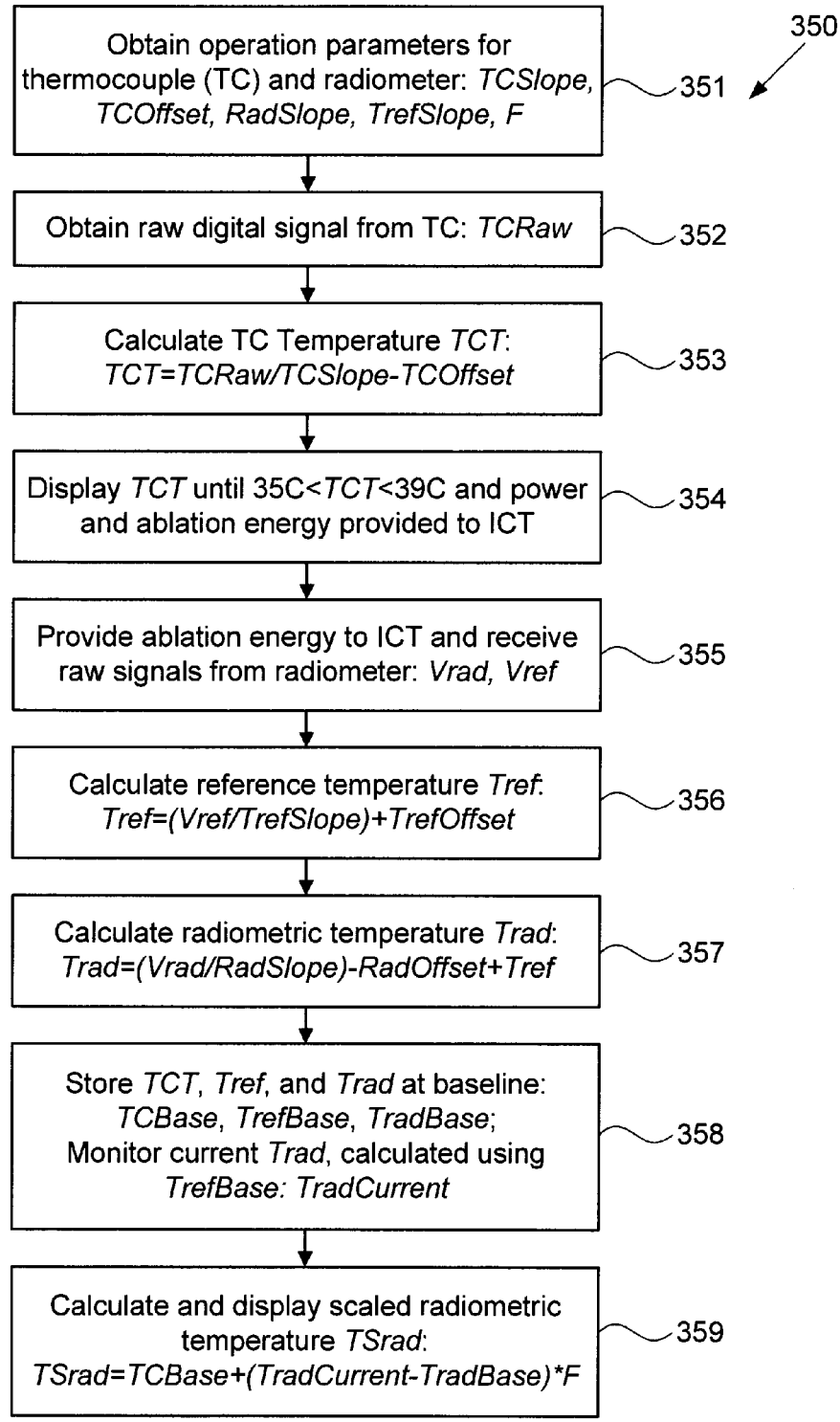
FIG. 3B illustrates steps in a method of calculating radiometric temperature using digital signals from a radiometer and a thermocouple and operation parameters.

Turning to FIG. 3B, the steps of method 350 of calculating radiometric temperature using digital signals from a radiometer and a thermocouple and operation parameters is described. The steps of the method may be executed by processor 210 based on temperature calculation module 233 stored in memory 230 (see FIG. 2A). While some of the signals and operation parameters discussed below are particular to a PIM and ICT configured for use with RF ablation energy, other signals and operation parameters may be suitable for use with a PIM and ICT configured for use with other types of ablation energy. Those skilled in the art will be able to modify the systems and methods provided herein for use with other types of ablation energy.

In FIG. 3B, processor 210 obtains from memory 230 the operation parameters for the thermocouple (TC) and the radiometer (step 351). These operation parameters may include, for example, TCSlope, which is the slope of the TC response with respect to temperature; TCOffset, which is the offset of the TC response with respect to temperature; RadSlope, which is the slope of the radiometer response with respect to temperature; TrefSlope, which is the slope of a reference temperature signal generated by the radiometer with respect to temperature; and F, which is a scaling factor.

Processor 210 then obtains via first I/O port 201 and opto-electronics 299 the raw digital signal from the thermocouple, TCRaw (step 352), and calculates the thermocouple temperature, TCT, based on TCRaw using the following equation (step 353):

$$TCT = \frac{TCRaw}{TCSlope} - TCOffset$$

Next, processor 210 causes temperature display 113 to display TCT until both of the following conditions are satisfied: TCT is in the range of 35° C. to 39° C., and ablation energy is being provided to the ICT (e.g., until step 306 of FIG. 3A). There are several reasons to display only the thermocouple temperature TCT, as opposed to the temperature calculated based on signal(s) from the radiometer, until both of these conditions are satisfied. First, if the temperature TCT measured by the thermocouple is less than 35° C., then based on instructions in decision module 234 the processor 210 interprets that temperature as meaning that the ICT is not positioned within a living human body, which would have a temperature of approximately 37° C. If the ICT is not positioned within a living human body, then it would be unsafe to provide power to the radiometer circuitry, as it may rapidly burn out if powered on in air as opposed to blood.

Processor 210 then provides ablation energy to the ICT, e.g., in accordance with step 306 described above, and receives via second I/O port 202 two raw digital signals from the radiometer: Vrad, which is a voltage generated by the radiometer based on the temperature adjacent the ICT; and Vref, which is a reference voltage generated by the radiometer (step 355). Processor 210 calculates the reference temperature Tref based on Vref using the following equation (step 356):

$$Tref = \frac{Vref}{TrefSlope} + TreOffset$$

Processor 210 also calculates the radiometric temperature Trad based on Vrad and Tref using the following equation (step 357):

$$Trad = \frac{Vrad}{RadSlope} - RadOffset + Tref$$

During operation of interface module 110, processor 210 may continuously calculate TCT, and also may continuously calculate Tref and Trad during times when ablation power is provided to the ICT (which is subject to several conditions discussed further herein). Processor 210 may store in memory 230 these values at specific times and/or continuously, and use the stored values to perform further temperature calculations. For example, processor 210 may store in memory 230 TCT, Tref, and Trad at baseline, as the respective values TCBase, TrefBase, and TradBase. The processor then re-calculates the current radiometric temperature TradCurrent based on the current Vrad received on second I/O port 202, but instead with reference to the baseline reference temperature TrefBase, using the following equation (step 358):

$$TradCurrent = \frac{Vrad}{RadSlope} - RadOffset + TrefBase$$

Processor 210 then calculates and causes temperature display 113 to display a scaled radiometric temperature TSrad for use by the clinician based on the baseline thermocouple temperature TCBase, the baseline radiometer temperature TradBase, and the current radiometer temperature TradCurrent, using the following equation (step 359):

$$TSrad = TCBase + (TradCurrent - TradBase) \times F$$

In this manner, interface module 110 displays for the clinician's use a temperature calculated based on signal(s) from the radiometer that is based not only on voltages generated by the radiometer and its internal reference, described further below with reference to FIGS. 6A-6B, but also on temperature measured by the thermocouple.

Figure 3C:
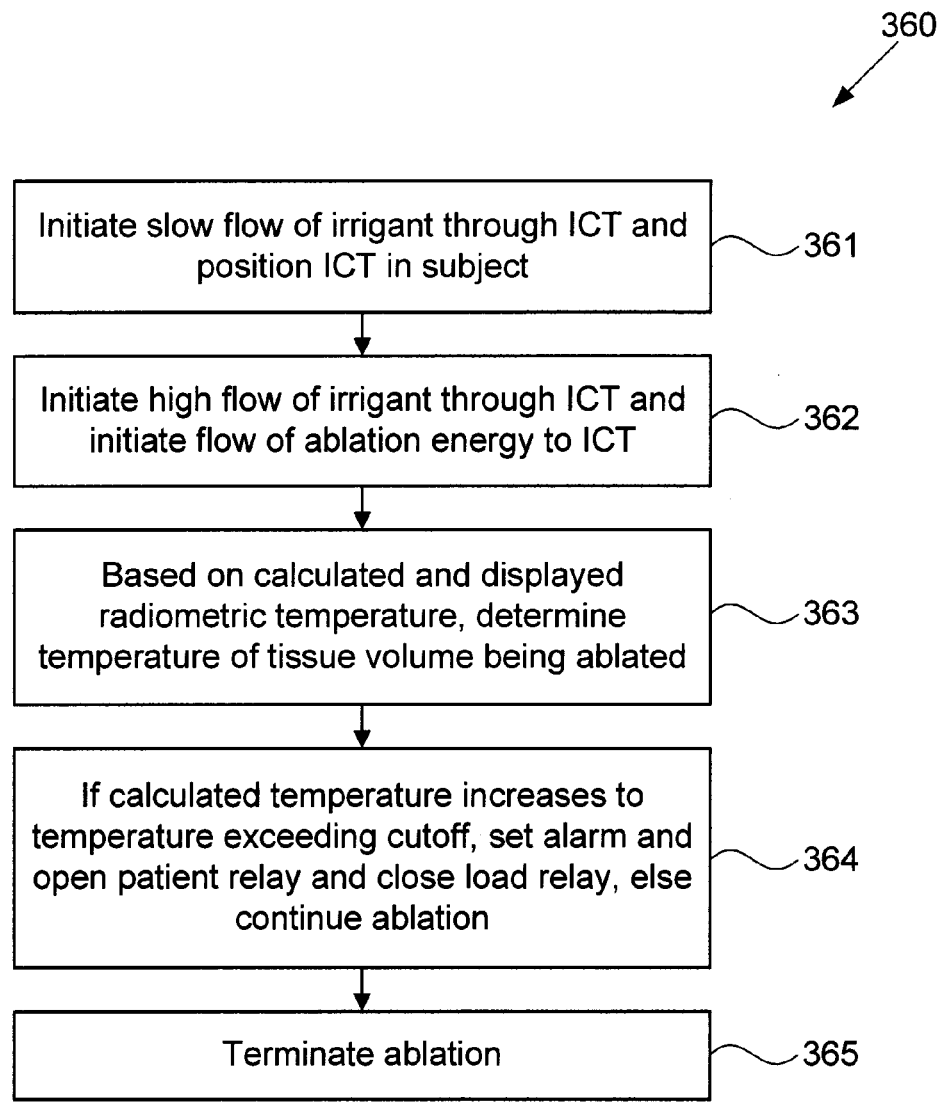
FIG. 3C illustrates steps in a method of controlling an ablation procedure using a temperature calculated based on signal(s) from a radiometer using the interface module of FIGS. 1A-2B.

With respect to FIG. 3C, method 360 of controlling an ablation procedure based on a temperature calculated based on signal(s) from a radiometer, e.g., as calculated using method 350 of FIG. 3B, and also based on safety parameters 232 and decision module 234 stored in memory 230 is described.

In FIG. 3C, a slow flow of irrigant is initiated through the ICT and the ICT is then positioned within the subject (step 361). For example, in embodiments for use with a Stockert 70 RF Generator, the generator may automatically initiate slow irrigant flow to the catheter tip by sending appropriate signals to a CoolFlow irrigant pumping system associated with the generator, responsive to actuation of the generator by the clinician.

Next, the clinician presses a button on the generator to start the flow of ablation energy to the ICT; this may cause the generator to initiate a high flow of irrigant to the ICT and generation of ablation energy following a 5 second delay (step 362). The interface module passes the ablation energy to the ICT via the patient relay, as described above with respect to step 306 of FIG. 3A.

Based on the calculated and displayed radiometric temperature (see methods 300 and 350 described above with respect to FIGS. 3A-3B), the clinician determines the temperature of the tissue volume that is being ablated by the ablation energy (step 363). By comparison, temperature measured by a thermocouple alone would provide little to no useful information during this stage of the procedure.

Interface module 110 may use the calculated radiometric temperature to determine whether the ablation procedure is being performed within safety parameters. For example, processor 210 may obtain safety parameters 232 from memory 230. Among other things, these safety parameters may include a cutoff temperature above which the ablation procedure is considered to be "unsafe" because it may result in perforation of the cardiac tissue being ablated, with potentially dire consequences. The cutoff temperature may be any suitable temperature below which one or more unsafe conditions may not occur, for example "popping" such as described below with respect to FIGS. 4C-4D, or tissue burning, but at which the tissue still may be sufficiently heated. One example of a suitable cutoff temperature is 85° C., although higher or lower cutoff temperatures may be used, e.g., 65° C., 70° C., 75° C., 80° C., 90° C., or 95° C. Instructions in decision module 234, also stored in memory 230, cause processor 210 to continuously compare the calculated radiometric temperature to the cutoff temperature, and if the radiometric temperature exceeds the cutoff temperature, the processor may set an alarm, open the patient relay, and close the load relay so as to return power to the IE via I/O port 204, thereby cutting off flow of ablation energy to the ICT (step 364 of FIG. 3C). Otherwise, the processor may allow the ablation procedure to proceed (step 364).

The ablation procedure terminates (step 365), for example, when the clinician presses the appropriate button on generator 130, or when the generator 130 automatically cuts of ablation energy at the end of a predetermined period of time.

Figure 4A:
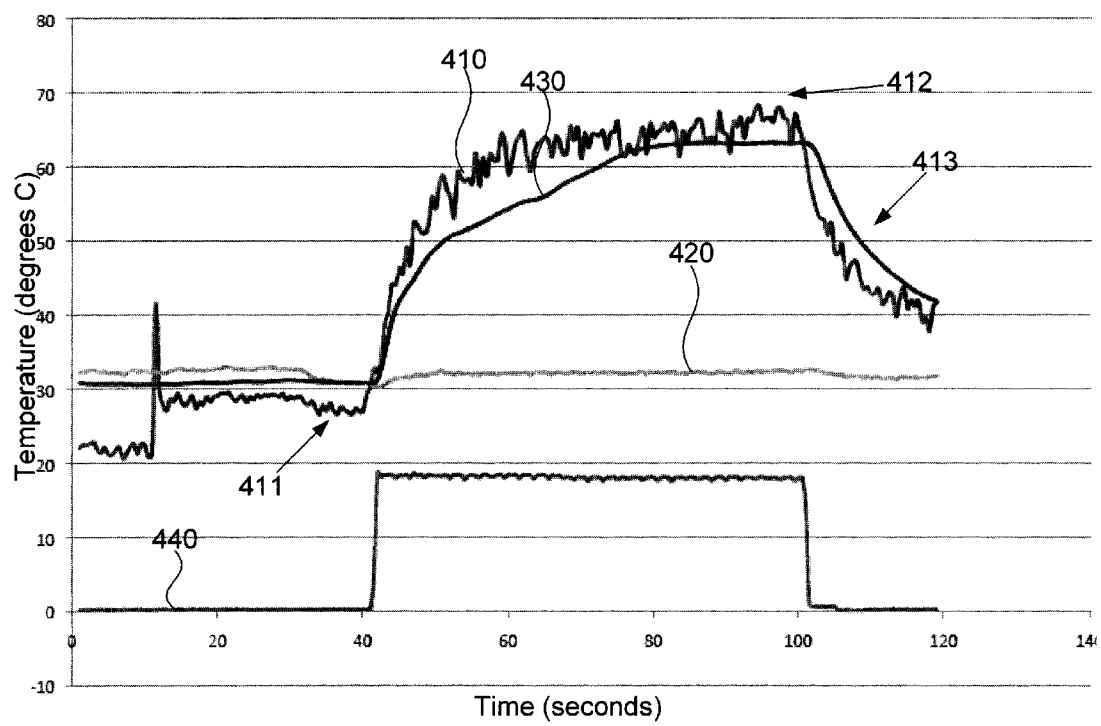
FIGS. 4A-4D illustrate data obtained during exemplary ablation procedures performed using the interface module of FIGS. 1A-2B.
Figure 4B:
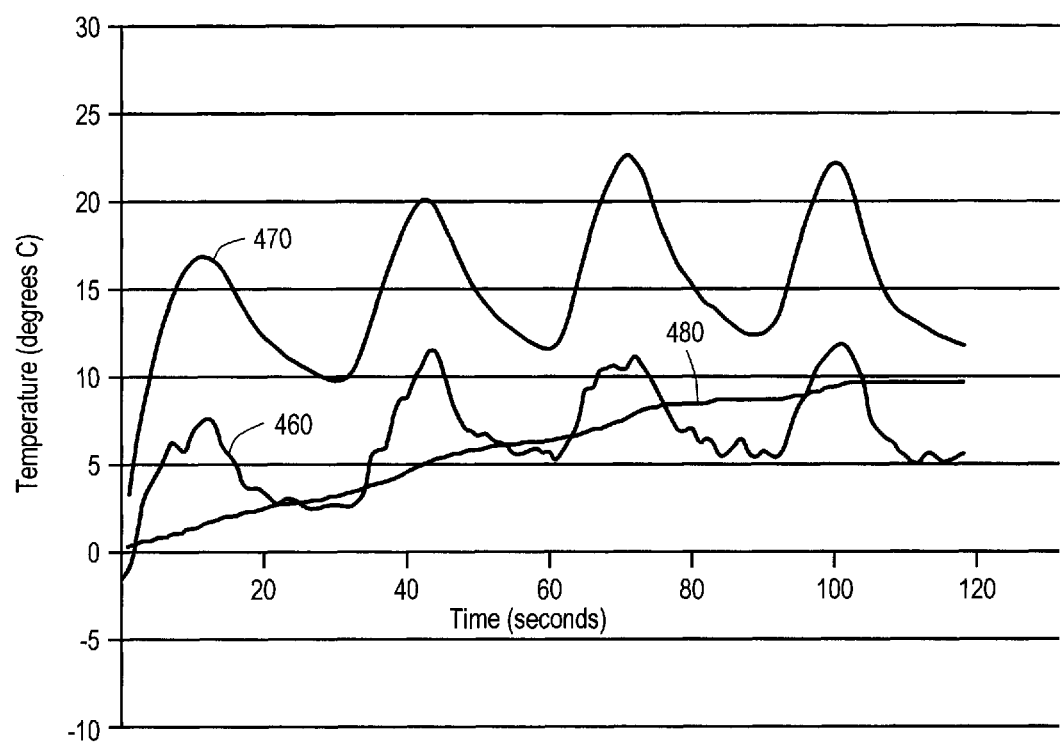

Referring now to FIGS. 4A-4B, illustrative data obtained during an ablation experiment using an interface module constructed in accordance with the present invention is described. This data was obtained using an unmodified Stockert EP Shuttle Generator with integrated irrigation pump, and a catheter including the PIM 121 and ICT 122 described further below with reference to FIGS. 5A-6B coupled to interface module 110. The ICT was placed against exposed thigh tissue of a living dog, and the Stockert EP Shuttle generator actuated so as to apply 20 W of RF energy for 60 seconds. A Luxtron probe was also inserted at a depth of 3 mm into the dog's thigh. Luxtron probes are considered to provide accurate temperature information, but are impractical for normal use in cardiac ablation procedures because such probes cannot be placed in the heart of a living being.

FIG. 4A illustrates the change over time in various signals collected during the ablation procedure. Signal 410 corresponds to scaled radiometric temperature TSrad; signal 420 corresponds to the thermocouple temperature; signal 430 corresponds to a temperature measured by the Luxtron probe; and signal 440 corresponds to the power generated by the Stockert EP Shuttle Generator.

As can be seen from FIG. 4A, power signal 440 indicates that RF power was applied to the subject's tissue beginning at a time of about 40 seconds and ending at a time of about 100 seconds. Radiometric temperature signal 410 indicates a sharp rise in temperature beginning at about 40 seconds, from a baseline in region 411 of about 28° C. to a maximum in region 412 of about 67° C., followed by a gradual fall in region 413 beginning around 100 seconds. The features of radiometric temperature signal 410 are similar to those of Luxtron probe signal 430, which similarly shows a temperature increase beginning around 40 seconds to a maximum value just before 100 seconds, and then a temperature decrease beginning around 100 seconds. This similarity indicates that the radiometric temperature has similar accuracy to that of the Luxtron probe. By comparison, thermocouple signal 420 shows a significantly smaller temperature increase beginning around 40 seconds, followed by a low-level plateau in the 40-100 second region, and then a decrease beginning around 100 seconds. The relatively weak response of the thermocouple, and the relatively strong and accurate response of the Luxtron thermocouple, indicate that an unmodified Stockert EP Shuttle Generator successfully may be retrofit using interface module 110 constructed in accordance with the principles of the present invention to provide a clinician with useful radiometric temperature information for use in an ablation procedure.

FIG. 4B illustrates signals obtained during a similar experimental procedure, but in which two Luxtron probes were implanted into the animal's tissue, the first at a depth of 3 mm and the second at a depth of 7 mm. The Stockert EP Shuttle generator was activated, and the RF power was manually modulated between 5 and 50 W using the power control knob on the front panel of the generator. In FIG. 4B, the radiometer signal is designated 460, the 3 mm Luxtron designated 470, and the 7 mm Luxtron designated 480. The radiometer and 3 mm Luxtron signals 460, 470 may be seen to have relatively similar changes in amplitude to one another resulting from the periodic heating of the tissue by RF energy. The 7 mm Luxtron signal 480 may be seen to have a slight periodicity, but far less modulation than do the radiometer and 3 mm Luxtron signals 460, 470. This is because the 7 mm Luxtron is sufficiently deep within the tissue that ablation energy substantially does not directly penetrate at that depth. Instead, the tissue at 7 mm may be seen to slowly warm as a function of time, as heat deposited in shallower portions of the tissue gradually diffuses to a depth of 7 mm.

A series of cardiac ablation procedures were also performed in living humans using the experimental setup described above with respect to FIGS. 4A-4B, but omitting the Luxtron probes. The humans all suffered from atrial flutter, were scheduled for conventional cardiac ablation procedures for the treatment of same, and consented to the clinician's use of the interface box and ICT during the procedures. The procedures were performed by a clinician who introduced the ICT into the individuals' endocardia using conventional methods. During the procedures, the clinician was not allowed to view the temperature calculated by the interface module. As such, the clinician performed the procedures in the same manner as they would have done with a system including a conventional RF ablation catheter directly connected to a Stockert EP-Shuttle generator. The temperature calculated by the interface module during the various procedures was made available for the clinician to review at a later time. The clinician performed a total of 113 ablation procedures on five humans using the above-noted experimental setup.

Figure 4C:
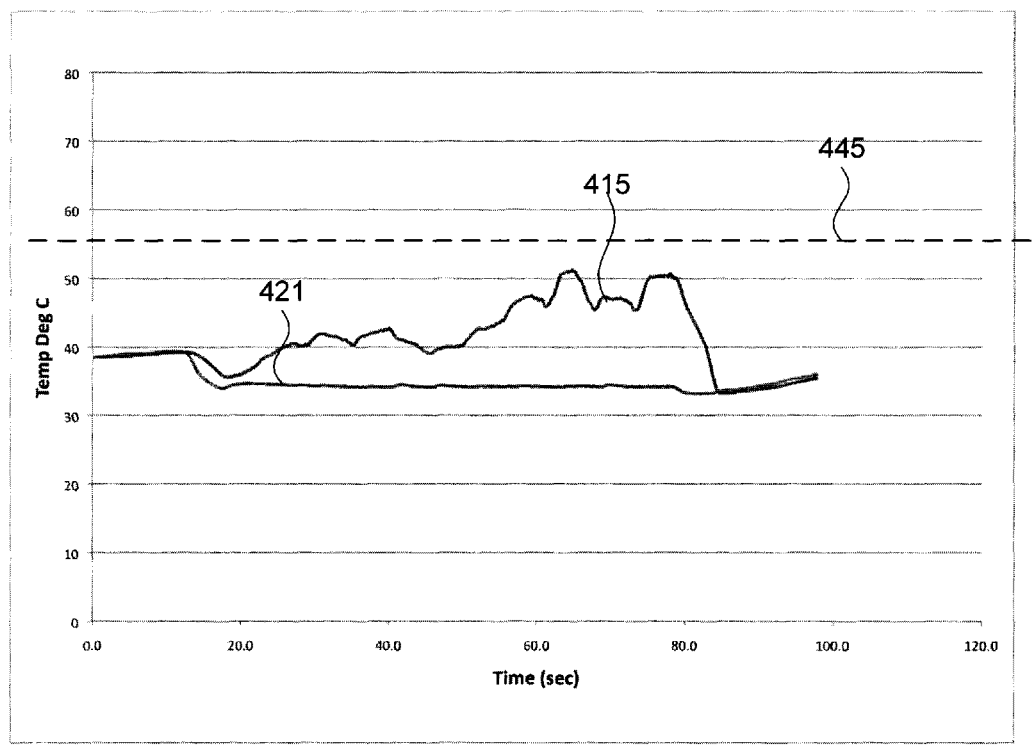
Figure 4D:
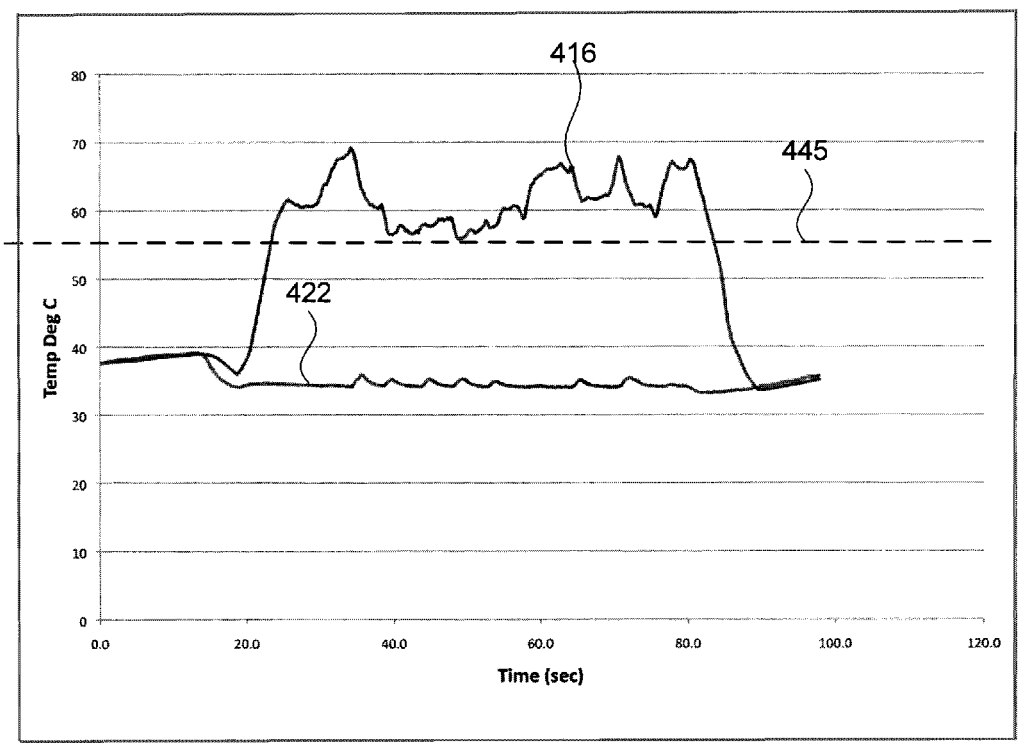

FIGS. 4C-4D illustrate data obtained during sequential ablation procedures performed on a single individual using the experimental setup. Specifically, FIG. 4C illustrates the change over time in the signal 415 corresponding to the scaled radiometric temperature TSrad, as well as the change over time in the signal 421 corresponding to the thermocouple temperature, during the tenth ablation procedure performed on the individual. During the procedure, about 40 W of RF power was applied to the individual's cardiac tissue for 60 seconds (between about 20 seconds and 80 seconds in FIG. 4C), and the clinician had a target temperature 445 of 55° C. to which it was desired to heat the cardiac tissue so as to sufficiently interrupt an aberrant pathway causing the individual's atrial flutter. It can be seen that the scaled radiometric temperature signal 415, which was subjected to data smoothing in FIG. 4C, varied between about 40° C. and 51° C. while RF power was applied. By comparison, as expected, the thermocouple temperature 421 provided essentially no useful information about the tissue temperature during the procedure. Notably, the clinician's target temperature 445 of 55° C. was never reached during the procedure, even though the clinician believed based on his or her perceptions of the procedure that such temperature had been reached. Because the target temperature 445 was not reached, the tissue was insufficiently heated during the procedure to interrupt an aberrant pathway. The failure to reach the target temperature may be attributed to insufficient contact or force between the ablative tip of the ICT and the individual's cardiac tissue, the condition of the cardiac surface, insufficient power, and the like.

FIG. 4D illustrates the change over time in signal 416 corresponding to TSrad, as well as the change over time in the signal 422 corresponding to the thermocouple temperature, during the eleventh ablation procedure performed on the same individual as in FIG. 4C. During this procedure, again about 40 W of RF power was applied to the individual's cardiac tissue for 60 seconds (between about 20 seconds and 80 seconds in FIG. 4D), and the clinician again had a target temperature 445 of 55° C. It can be seen that the scaled radiometric signal 416, again subject to data smoothing, varied between about 55 C and 70° C. while RF power was applied, while the thermocouple temperature 421 again provided essentially no useful information. Here, the clinician attributed the higher temperature tissue temperature achieved during the ablation to better contact between the ablative tip of the ICT and the individual's cardiac tissue. However, it can be seen that even while RF power was being applied to the tissue, the temperature varied relatively rapidly over time, e.g., from about 70° C. at about 35 seconds, to about 56° C. at 40 seconds, which may be attributed to variations in the quality of contact between the ICT and the individual's cardiac tissue.

The results of the ablation procedures performed on the five individuals are summarized in the following table:

|  | Total | % of Total Ablation |
|---|---|---|
| Number of patients | 5 |  |
| Number of ablations | 113 |  |
| Number of ablations that did not reach target temperature of 55° C. | 50 | 44% |
| Number of ablations that reached high temperature cutoff of 95° C. | 13 | 12% |
| Number of pops | 3 | 3% |
| Number of successful treatments of atrial flutter | 5 | 100% |

As can be seen from the above table, 44% of the ablation procedures did not reach the clinician's target tissue temperature of 55° C. As such, it is likely that this percentage of the procedures resulted in insufficient tissue heating to interrupt aberrant pathway(s). However, although many of the ablation procedures failed, the clinician repeated the ablation procedures a sufficient number of times to achieve 100% treatment of the individuals' atrial flutter. It is believed that displaying the calculated temperature to the clinician during ablation procedures would enable the clinician to far more accurately assess the quality of contact between the ablative tip of the ICT and the individual's cardiac tissue, and thus to sufficiently heat the tissue above the target temperature for a desired period of time, and thus reduce the clinicians' need to repeatedly perform numerous ablation procedures on the same subject so as to achieve the desired treatment.

As shown in the above table, 12% of the ablation procedures triggered the high temperature cutoff such as illustrated in FIG. 3C. Here, the cutoff temperature was defined to be 95° C. However, it was observed that at this cutoff temperature, "pops" formed during three of the ablation procedures. A "pop" occurs when the blood boils because of excessive localized heating caused by ablation energy, which results in formation of a rapidly expanding bubble of hot gas that may cause catastrophic damage to the cardiac tissue. It is believed that a lower cutoff temperature, e.g., 85° C., may inhibit formation of such "pops."

Additional components that may be used in conjunction with interface module 110 of the present invention, e.g., PIM 121 and ICT 122 of catheter 120, are now briefly described with reference to FIGS. 5A-6B.

Figure 5A:
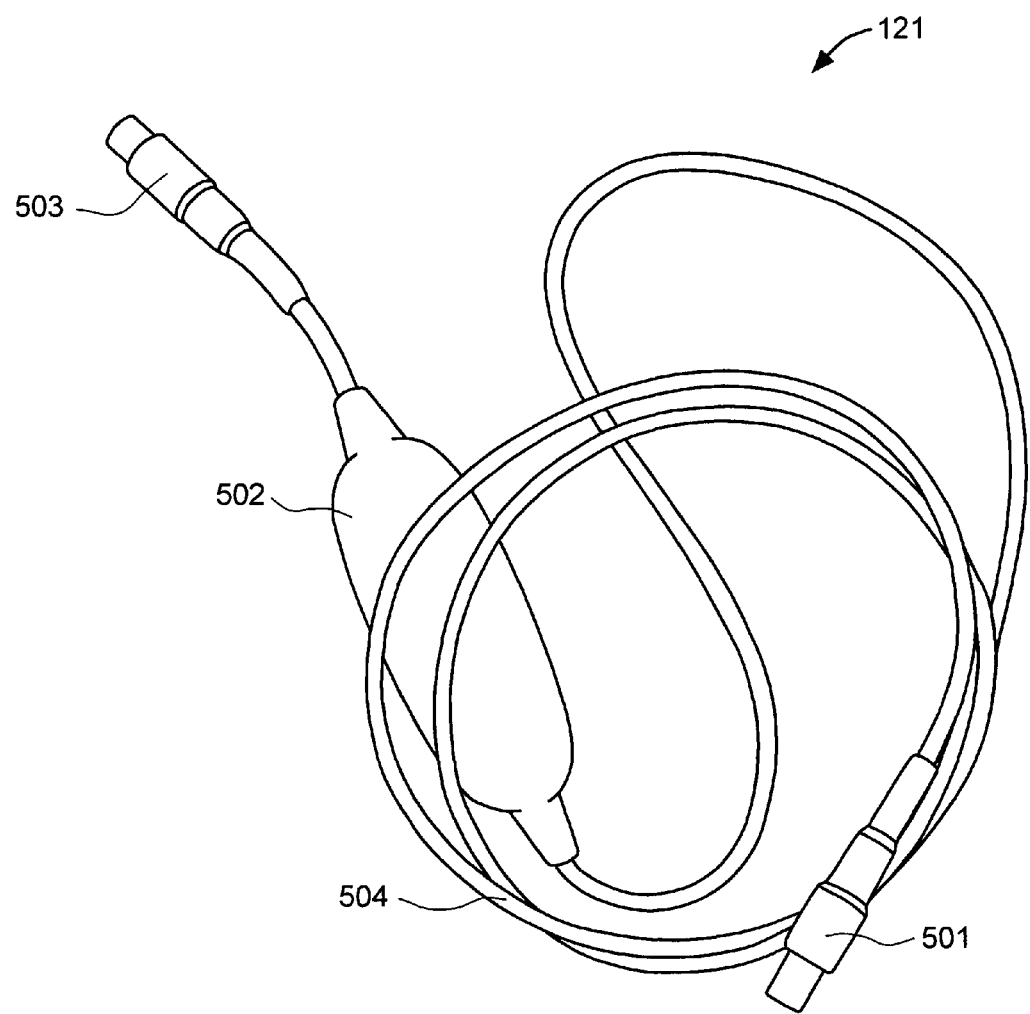
FIG. 5A illustrates a plan view of an exemplary patient interface module (PIM) associated with an integrated catheter tip (ICT) for use with the interface module of FIGS. 1A-2B.
Figure 5B:
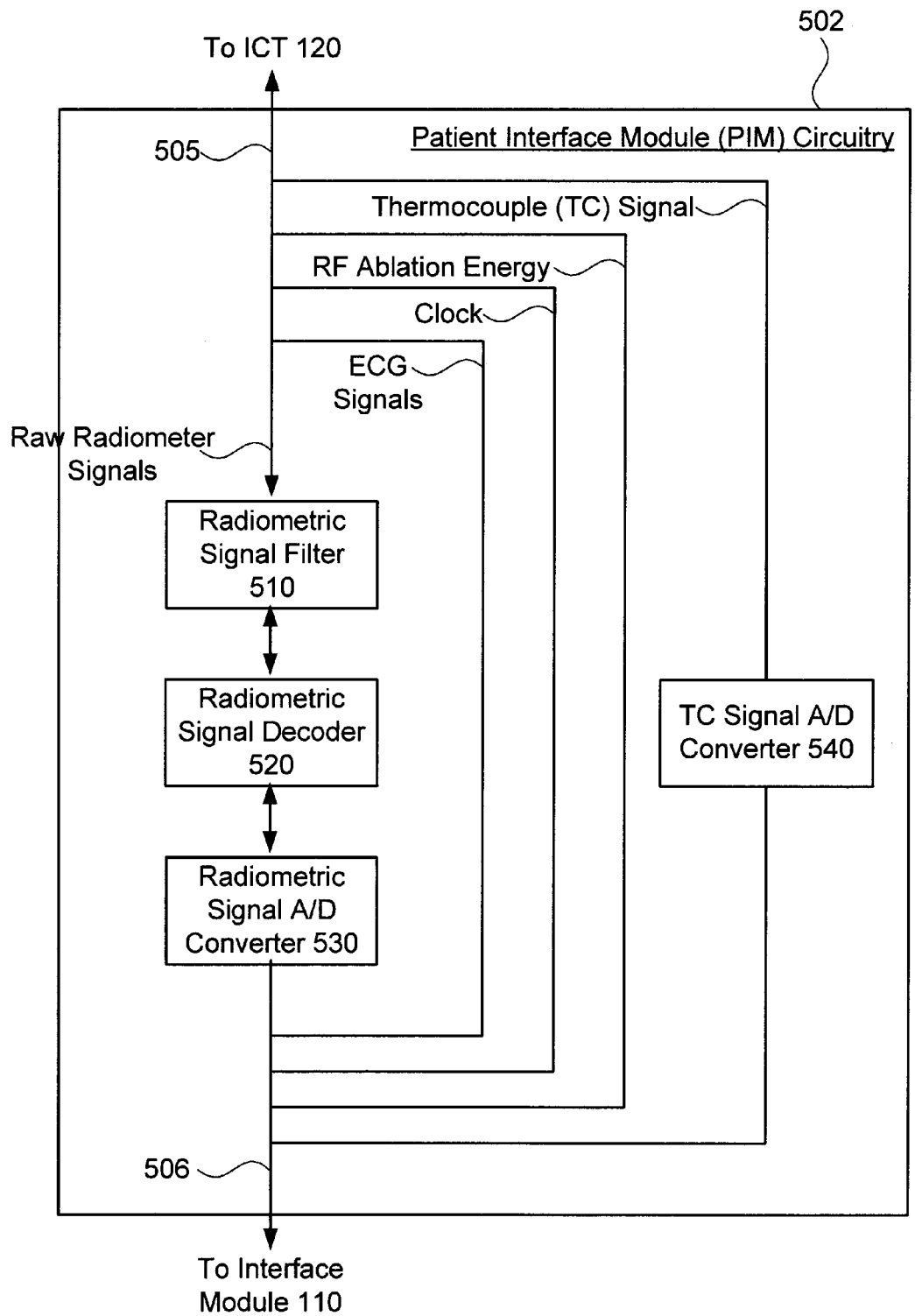
FIG. 5B schematically illustrates selected internal components of the PIM of FIG. 5A, according to some embodiments of the present invention.
Figure 6A:
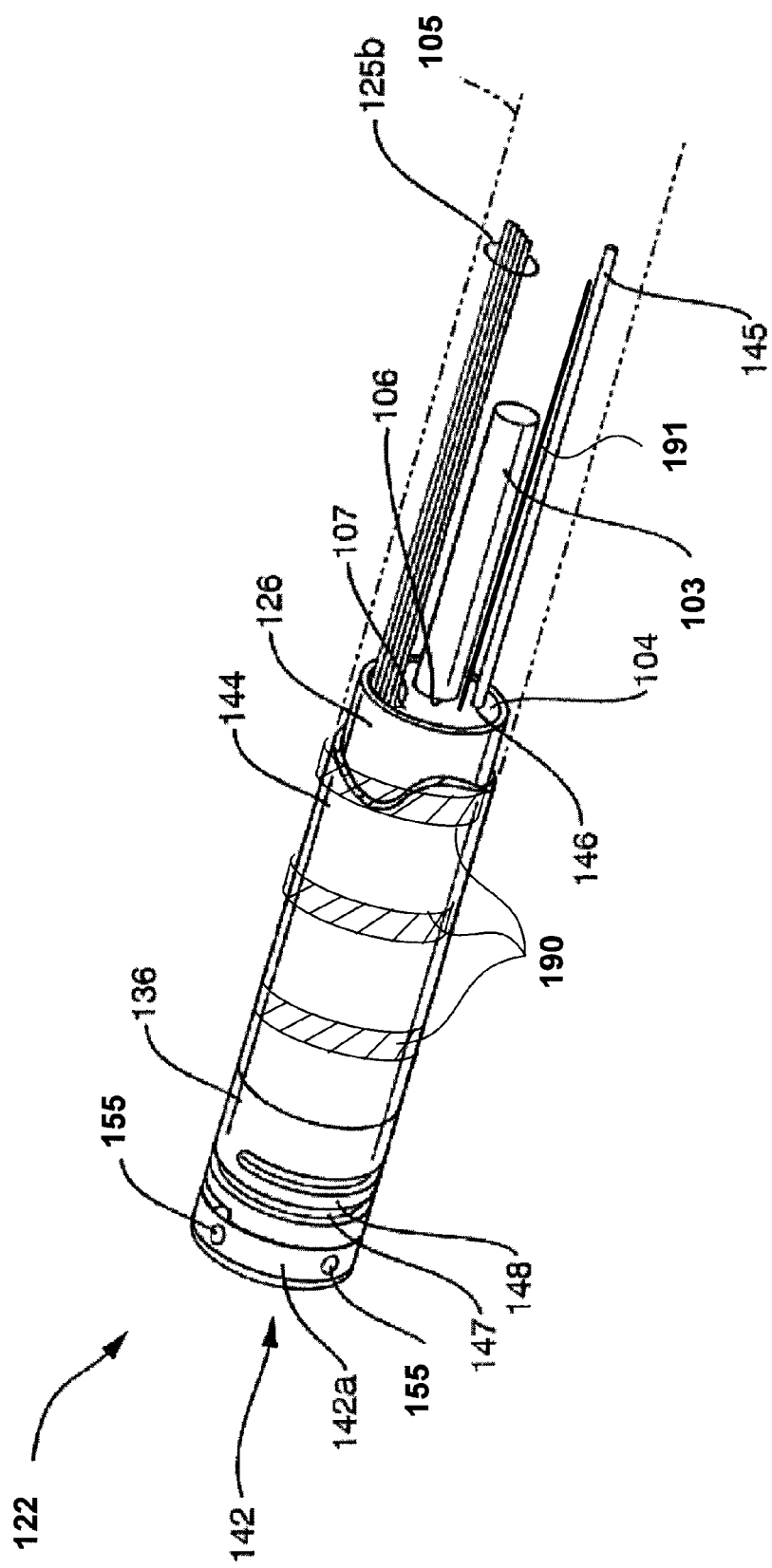
FIGS. 6A-6B respectively illustrate perspective and exploded views of an exemplary integrated catheter tip (ICT) for use with the interface module of FIGS. 1A-2B and the PIM of FIGS. 5A-5B, according to some embodiments of the present invention.
Figure 6B:
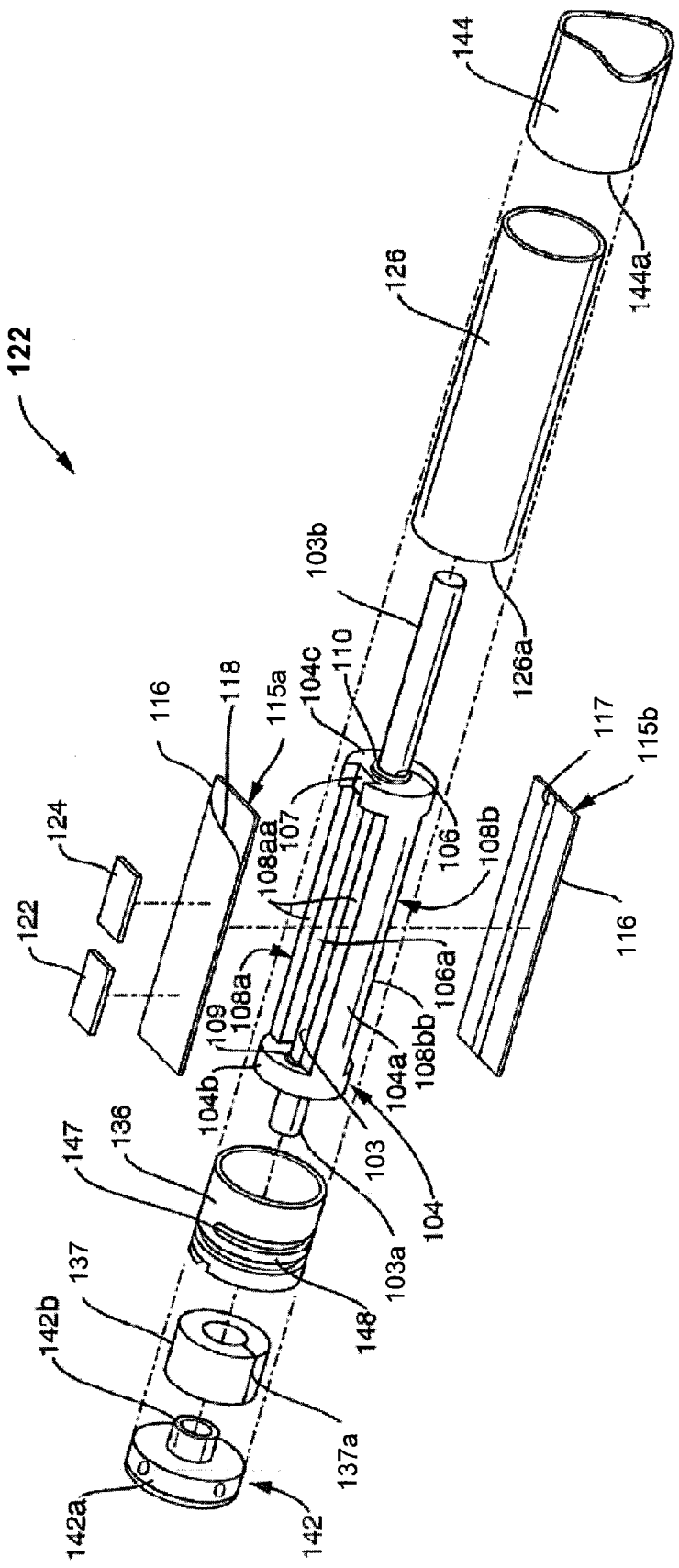

In FIG. 5A, patient interface module (PIM) 121 that may be associated with the integrated catheter tip (ICT) described further below with respect to FIGS. 6A-6B is described. PIM 121 includes interface module connector 501 that may be connected to front panel 111 of interface module 110, as described with reference to FIG. 1A; PIM circuitry 502, which will be described in greater detail below with reference to FIG. 5B; ICT connector 503 that may be connected to catheter 120; and PIM cable 504 that extends between interface module connector 501 and PIM circuitry 502. PIM 121 is preferably, but not necessarily, designed to remain outside the sterile field during the ablation procedure, and optionally is reusable with multiple ICT's.

FIG. 5B schematically illustrates internal components of PIM circuitry 502, and includes first I/O port 505 configured to be coupled to catheter 120, e.g., via ICT connector 503, and second I/O port 506 configured to be coupled to interface module 110, e.g., via PIM cable 504 and interface module connector 501.

PIM circuitry 502 receives on first I/O port 505 an analog thermocouple (TC) signal, raw analog radiometer signals, and analog ECG signals from catheter 120. PIM circuitry 502 includes TC signal analog-to-digital (A/D) converter 540 that is configured to convert the analog TC signal to a digital TC signal, and provide the digital TC signal to interface module 110 via second I/O port 506. PIM circuitry 502 includes a series of components configured to convert the raw analog radiometer signals into a usable digital form. For example, PIM circuitry may include radiometric signal filter 510 configured to filter residual RF energy from the raw analog radiometer signals; radiometric signal decoder 520 configured to decode the filtered signals into analog versions of the Vref and Vrad signals mentioned above with reference to FIG. 3B; and radiometric signal A/D converter 530 configured to convert the analog Vref, Vrad signals into digital Vref, Vrad signals and to provide those digital signals to second I/O port for transmission to interface module 110. PIM circuitry 502 also passes through the ECG signals to second I/O port 506 for transmission to interface module 110.

On second I/O port 506, PIM circuitry 502 receives RF ablation energy from generator 130 (e.g., a Stockert EP-Shuttle or 70 RF Generator) via interface module 110. PIM circuitry 502 passes that RF ablation energy through to catheter 120 via first I/O port 505. PIM circuitry 502 also receives on second I/O port 506 a clock signal generated by RF circuitry within interface module 110, as described further above with reference to FIG. 2B, and passes through the clock signal to first I/O port 505 for use in controlling microwave circuitry in ICT 122, as described below.

Referring now to FIGS. 6A-6B, an exemplary integrated catheter tip (ICT) 122 for use with the interface module 110 of FIGS. 1A-2B and the PIM of FIGS. 5A-5B is described.

Further detail on components of ICT 122 may be found in U.S. Pat. No. 7,769,469 to Carr, the entire contents of which are incorporated herein by reference, as well as in U.S. Patent Publication No. 2010/0076424, also to Can ("the Can publication"), the entire contents of which are incorporated herein by reference. The device described in the aforementioned patent and publication do not include a thermocouple or ECG electrodes, which preferably are included in ICT 122 configured for use with interface module 110.

As described in the Can publication and as depicted in FIGS. 6A-6B, ICT 122 includes an inner or center conductor 103 supported by a conductive carrier or insert 104. Carrier 104 may be formed from a cylindrical metal body having an axial passage 106 that receives conductor 103. Upper and lower sectors of that body extending inward from the ends may be milled away to expose passage 106 and conductor 103 therein and to form upper and lower substantially parallel flats 108a and 108b. Flat 108a may include coplanar rectangular areas 108aa spaced on opposite sides of conductor 103 near the top thereof. Likewise, flat 108b may include two coplanar rectangular areas 108bb spaced on opposite sides of conductor 103 near the bottom thereof. Thus, carrier 104 may include center segment 104a containing the flats and distal and proximal end segments 104b and 104c, respectively, which remain cylindrical, except that a vertical groove 107 may be formed in proximal segment 104c.

Center conductor 103 may be fixed coaxially within passage 106 by means of an electrically insulating collar or bushing 109, e.g. of PTFE, press fit into passage 106 at distal end segment 104b of the carrier and by a weld to the passage wall or by an electrically conductive collar or bushing (not shown) at the carrier proximal segment 104c. This causes a short circuit between conductor 103 and carrier 104 at the proximal end of the carrier, while an open circuit may be present therebetween at the distal end of the carrier. In the carrier center segment 104a, the walls 106a of passage 106 may be spaced from center conductor 103. This forms a quarter wave stub S, as described in greater detail in U.S. Pat. No. 7,769,469 and U.S. Patent Publication No. 2010/0076424. Conductor 103 includes distal end segment 103a which extends beyond the distal end of carrier 104 a selected distance, and a proximal end segment 103b which extends from the proximal end of ICT 122 and connects to the center conductor of cable 105 configured to connect to PIM 121.

As illustrated in FIG. 6B, mounted to the upper and lower flats 108a and 108b of carrier 104 is a pair of opposed, parallel, mirror-image, generally rectangular plates 115a and 115b. Each plate 115a, 115b may include a thin, e.g. 0.005 in., substrate 116 formed of an electrically insulating material having a high dielectric constant. Printed, plated or otherwise formed on the opposing or facing surfaces of substrates 116 are axially centered, lengthwise conductive strips 117, preferably 0.013-0.016 mm wide, which extend the entire lengths of substrates 116. Also, the opposite or away-facing surfaces of substrates 116 are plated with conductive layers 118, e.g. of gold. The side edges of layers 118 wrap around the side edges of the substrates.

When the ICT is being assembled, plate 115a may be seated on the upper flat 108a of carrier 104 and the lower plate 115b is likewise seated on the lower flat 108b so that the center conductor 103 is contacted from above and below by the conductive strips 117 of the upper and lower plates and the layer 118 side edges of those plates contact carrier segment 104a. A suitable conductive epoxy or cement may be applied between those contacting surfaces to secure the plates in place.

At least one of the plates, e.g. plate 115a, functions also as a support surface for one or more monolithic integrated circuit chips (MMICs), e.g. chips 122 and 124. The chip(s) may include a coupling capacitor connected by a lead (not shown) to center conductor 103 and the usual components of a radiometer such as a Dicke switch, a noise source to provide a reference temperature, amplifier stages, a band pass filter to establish the radiometer bandwidth, additional gain stages if needed, a detector and buffer amplifier. Due to the relatively small profile of the present ICT 122, the above circuit components may be arranged in a string of four chips. The chip(s) may be secured to the metal layer 118 of plate 115a by a suitable conductive adhesive so that that layer which, as described above, is grounded to the insert 104 may function as a ground plane for those chips. The plates also conduct heat away from the chips to conductor 103 and carrier 104. Various leads (not shown) connect the chips to each other and other leads 125b extend through carrier slot 107 and connect the last chip 124 in the string, i.e. the radiometer output, to corresponding conductors of cable 105 leading to PIM 121.

A tubular outer conductor 126 may be slid onto carrier 104 from an end thereof so that it snugly engages around the carrier with its proximal and distal ends coinciding with the corresponding ends of the carrier (not shown). The conductor 126 may be fixed in place by a conductive epoxy or cement applied around the carrier segments 104b and 104c.

ICT 122 also may include an annular dielectric spacer 137, e.g. of PTFE, which is centered on the distal end of carrier 104 and surrounds the conductor segment 103a. The spacer may have a slit 137a enabling it to be engaged around that conductor segment from the side thereof. The spacer 137 may be held in place by a conductive collar 136 which encircles the spacer and is long enough to slidably engage over a distal end segment of outer conductor 126. The collar 136 may be press fit around that conductor and carrier segment 104b to hold it in place and to electrically connect all those elements.

The distal end of the ICT 122 may be closed off by conductive tip 142 which, in axial section, may be T shaped. That is, the tip 142 may have discoid head 142a that forms the distal end of the ICT and an axially extending tubular neck 142b. The conductor segment 103a is sufficiently long to extend beyond the distal end of the spacer 137 into the axial passage in neck 104b. The tip may be secured in place by conductive adhesive applied around the distal end of conductor segment 103a and at the distal end or edge of collar 136. When the tip is in place, the conductor segment 103a and tip 104 form a radiometric receiving antenna, as described in greater detail in U.S. Pat. No. 7,769,469 and U.S. Patent Publication No. 2010/0076424.

ICT 122 may further include dielectric sheath 144 which may be engaged over the rear end of outer conductor 126 and slid forwardly until its distal end 144a is spaced a selected distance behind the distal end of tip 142. The conductors 103 and 126 of ICT 122 form an RF transmission line terminated by the tip 104. When the ICT 122 is operative, the transmission line may radiate energy for heating tissue only from the uninsulated segment of the probe between tip 104 and the distal end 144a of the sheath 144. That segment thus constitutes an RF ablation antenna.

The proximal ends of the center conductor segment 103b, outer conductor 126 and sheath 144 may be connected, respectively, to the inner and outer conductors and outer sheath of cable 105 that leads to PIM 121. Alternatively, those elements may be extensions of the corresponding components of cable 105. In any event, that cable 105 connects the center conductor 103 to the output of a transmitter which transmits a RF heating signal at a selected heating frequency, e.g. 500 GHz, to the RF ablation antenna.

As illustrated in FIG. 6A, ICT 122 further may include first, second, and third ECG electrodes 190 disposed on the outside of sheath 144, as well as a thermocouple 191 positioned so as to detect the temperature of blood or tissue in contact with ICT 122. Signals generated by electrodes 190 and thermocouple 191 may be provided along cable 105 connected to PIM 121.

If desired, cable 105 further may include probe steering wire 145 whose leading end 145a may be secured to the wall of a passage 146 in carrier segment 104c.

Preferably, helical through slot 147 is provided in collar 136 as shown in FIGS. 6A-6B. The collar material left between the slot turns essentially forms helical wire 148 that bridges spacer 137. Wire 148 is found to improve the microwave antenna pattern of the radiometric receiving antenna without materially degrading the RF heating pattern of the RF ablation antenna.

The inner or center conductor 103 may be a solid wire, or preferably is formed as a tube that enables conductor 103 to carry an irrigation fluid or coolant to the interior of probe tip 142 for distribution therefrom through radial passages 155 in tip head 142a that communicate with the distal end of the axial passage in tip neck 142b.

When plates 115a and 115b are seated on and secured to the upper and lower flats 108a and 108b, respectively, of carrier 104, conductive strips 117, 117 of those members may be electrically connected to center conductor 103 at the top and bottom thereof so that conductor 103 forms the center conducts for of a slab-type transmission line whose ground plane includes layers 118, 118.

When ablation energy is provided to ICT 122, a microwave field exists within the substrate 116 and is concentrated between the center conductor 103 and layers 118, 118. Preferably, as noted here, conductive epoxy is applied between conductor 103 and strips 117 to ensure that no air gaps exist there because such a gap would have a significant effect on the impedance of the transmission line as the highest field parts are closest to conductor 103.

Plates 115a, 115b and conductor 103 segment together with carrier 104 form a quarter wave ($\lambda_R/4$) stub S that may be tuned to the frequency of radiometer circuit 124, e.g. 4 GHz. The quarter wave stub S may be tuned to the center frequency of the radiometer circuit along with components in chips 122, 124 to form a low pass filter in the signal transmitting path to the RF ablation antenna, while other components of the chips form a high pass or band pass filter in the signal receiving path from the antenna to the radiometer. The combination forms a passive diplexer D which prevents the lower frequency transmitter signals on the signal transmitting path from antenna T from reaching the radiometer, while isolating the path to the transmitter from the higher frequency signals on the signal receiving path from the antenna.

The impedance of the quarter wave stub S depends upon the K value and thickness t of substrates 116 of the two plates 115a, 115b and the spacing of center conductor 103 from the walls 106a, 106a of passage 106 in the carrier center segment 104a. Because the center conductor 103 is not surrounded by a ceramic sleeve, those walls can be moved closer to the center conductor, enabling accurate tuning of the suspended substrate transmission line impedance while minimizing the overall diameter of the ICT 122. As noted above, the length of the stub S may also be reduced by making substrate 116 of a dielectric material which has a relatively high K value.

In one working embodiment of the ICT 122, which is only about 0.43 in. long and about 0.08 in. in diameter, the components of the ICT have the following dimensions:

| Component | Dimension (inches) |
| --- | --- |
| Conductor 103 | 0.020 outer diameter |
| | 0.016 inner diameter (if hollow) |
| Substrate 116 (K-9.8) | 0.065 wide; thickness t = 0.005 |
| Strips 117 | 0.015 wide |
| Air gap between 103 and each 106a | 0.015 |

Thus, the overall length and diameter of the ICT 122 may be relatively small, which is a useful feature for devices configured for percutaneous use.

While various illustrative embodiments of the invention are described above, it will be apparent to one skilled in the art that various changes and modifications may be made herein without departing from the invention. For example, although the interface module has primarily been described with reference for use with an RF electrosurgical generator and the PIM and ICT illustrated in FIGS. 5A-6B, it should be understood that the interface module suitably may be adapted for use with other sources of ablation energy and other types of radiometers. Moreover, the radiometer may have components in the ICT and/or the PIM, and need not necessarily be located entirely in the ICT. Furthermore, the functionality of the radiometer, ICT, and/or PIM optionally may be included in the interface module. The appended claims are intended to cover all such changes and modifications that fall within the true spirit and scope of the invention.

What is claimed is:

1. A method of determining a temperature and facilitating ablation of tissue of a subject, comprising:
    positioning a catheter of an ablation system at a target anatomical location of a subject, the catheter comprising an integrated catheter tip positioned along a distal end of the catheter, the integrated catheter tip comprising a radiofrequency electrode, a radiometer and a temperature-measurement device;
    determining a temperature of a tissue of the subject at a depth relative to a surface of the tissue based on, at least, a signal generated by the radiometer, a signal generated by the temperature-measurement device and operation parameters for the radiometer and the temperature-measurement device; and
    delivering radiofrequency energy to the tissue of the subject by activating a generator to provide energy to the radiofrequency electrode.

2. The method of claim 1, further comprising monitoring electrical activity of the subject using at least one electrocardiogram electrode, wherein the at least one electrocardiogram electrode is positioned along the integrated catheter tip.

3. The method of claim 1, further comprising operatively coupling the ablation system to an electrophysiology monitoring system.

4. The method of claim 1, wherein positioning the catheter at a target anatomical location of the subject comprises manipulating a steerable catheter or a steerable outer sheath.

5. The method of claim 1, further comprising displaying the determined temperature of the tissue of the subject on a display.

6. The method of claim 1, further comprising deactivating the radiofrequency electrode when the determined temperature of the tissue of the subject exceeds a threshold high temperature level.

7. The method of claim 1, wherein the operation parameters for the radiometer comprise a slope and an offset describing a temperature response of the radiometer, and wherein the operation parameters for the temperature-measurement device comprise a slope and an offset describing a temperature response of the temperature-measurement device.

8. A method of determining a temperature and facilitating ablation of tissue of a subject, comprising:
    determining a temperature of a tissue of a subject at a depth relative to the tissue's surface based on, at least, a signal generated by a radiometer and a signal generated by a temperature-measurement device, the radiometer and the temperature-measurement device being positioned at a distal end of a catheter; and
    delivering energy to the tissue of the subject by activating an ablation member positioned at the distal end of the catheter.

9. The method of claim 8, further comprising delivering irrigation fluid to a fluid passage of the catheter and through at least one irrigation fluid port of the catheter to cool tissue adjacent the ablation member.

10. The method of claim 8, further comprising monitoring electrical activity of the subject using at least one electrocardiogram electrode, wherein the at least one electrocardiogram electrode is positioned at the distal end of the catheter.

11. The method of claim 8, further comprising operatively coupling the ablation system to an electrophysiology monitoring system.

12. The method of claim 8, further comprising displaying the determined temperature of the tissue on a display.

13. The method of claim 8, wherein determining the temperature is additionally based on, at least in part, operation parameters for the radiometer and the temperature-measurement device, wherein the operation parameters for the radiometer comprise a slope and an offset describing a temperature response of the radiometer, and wherein the operation parameters for the temperature-measurement device comprise a slope and an offset describing a temperature response of the temperature-measurement device.

14. The method of claim 8, wherein the ablation member comprises one of a radiofrequency electrode, a microwave ablation member, a cryoablation member and an ultrasound ablation member.

15. A method of determining a temperature and facilitating ablation of tissue of a subject, comprising:
    determining a temperature of a tissue of the subject at a depth relative to the tissue's surface based on, at least, a signal generated by a radiometer and a signal generated by a temperature-measurement device configured to detect a temperature along a portion of a catheter, the catheter configured for contact with a surface of the tissue; and
    delivering energy to the tissue of the subject by activating an ablation member positioned on the catheter.

16. The method of claim 15, further comprising delivering irrigation fluid to a fluid passage of the catheter and through at least one irrigation fluid port positioned at a tip of the catheter to cool tissue adjacent the ablation member.

17. The method of claim 15, further comprising monitoring electrical activity of the subject using at least one electrocardiogram electrode.

18. The method of claim 15, further comprising displaying the determined temperature of the tissue on a display.

19. The method of claim 15, wherein determining the temperature is additionally based on, at least in part, operation parameters for the radiometer and the temperature-measurement device, wherein the operation parameters for the radiometer comprise a slope and an offset describing a temperature response of the radiometer, and wherein the operation parameters for the temperature-measurement device comprise a slope and an offset describing a temperature response of the temperature-measurement device.

20. The method of claim 15 wherein the ablation member comprises one of a radiofrequency electrode, a microwave ablation member, a cryoablation member and an ultrasound ablation member.

* * * * *